(12) United States Patent
Egland et al.

(10) Patent No.: US 10,001,484 B2
(45) Date of Patent: Jun. 19, 2018

(54) REAGENTS AND METHODS FOR BREAST CANCER DETECTION

(71) Applicant: Sanford Health, Sioux Falls, SD (US)

(72) Inventors: Kristi Egland, Sioux Falls, SD (US); Rick Evans, Sioux Falls, SD (US); James Pottala, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 0 days. days.

(21) Appl. No.: 14/660,423

(22) Filed: Mar. 17, 2015

(65) Prior Publication Data

US 2015/0268241 A1 Sep. 24, 2015

Related U.S. Application Data

(60) Provisional application No. 61/954,914, filed on Mar. 18, 2014.

(51) Int. Cl.
*C07K 4/00* (2006.01)
*G01N 33/574* (2006.01)
*G01N 33/564* (2006.01)

(52) U.S. Cl.
CPC ..... *G01N 33/57415* (2013.01); *G01N 33/564* (2013.01)

(58) Field of Classification Search
None
See application file for complete search history.

(56) References Cited

PUBLICATIONS

Tang et al (Clin Vaccine Immunol, 2010, 17(12): 1903-1908).*
Invitrogen ProtoArray Human Protein Microarray (v5.0 Protein-Protein Interaction (PPI) KIT Manual (2010).*
Han et al (PLOS ONE, 2012, 7(2): 1-6).*
Postow et al (NEJM, 2012, 366(10): 925-931).*
Agnantis, "Tumor markers. An update approach for their prognostic significance. Part I. In Vivo," PubMed PMID 14758728, vol. 17, No. 6, pp. 609-618, 2003 (abstract).
Akaike, "Information Theory and an Extension of the Maximum Likelihood Principle," In: Kotz S, Johnson NL, editors. Breakthroughs in Statistics. Springer Series in Statistics, Springer New York, p. 610-24, 1992.
American Cancer Society, "Find Support & Treatment, Mammograms and Other Breast Imaging Procedures," Available from: http://www.cancer.org/Treatment/UnderstandingYourDiagnosis/ExamsandTestDescriptions/MammogramsandOtherBreastImagingProcedures/mammograms-and-other-breast-imaging-procedures-having-a-mammogram, 2012.
Anderson, et al. "Protein Microarrays signature of Autoantibody Biomarkers for the early detection breast cancer," Journal of Proteome Research, vol. 10, No. 1, pp. 85-96, 2011.
Arciero , et al., "Functional relationship and gene ontology classification of breast cancer biomarkers," Int J Biol Markers, vol. 18, No. 4, pp. 241-272, 2003.

Barlow, et al., "Continuous and discontinuous protein antigenic determinants," Nature, vol. 322, No. 6081, pp. 747-748, PubMed PMID: 2427953, 1986.
Bendtsen, et al., "Improved prediction of signal peptides: SignalP 3.0.," J Mol Biol, vol. 340, No. 4, pp. 783-795, doi: 10.1016/j.jmb. 2004.05.028. PubMed PMID: 15223320, 2004.
Bergstralh, et al., "Computerized matching of cases to controls," Rochester, MN: Mayo Clinic Department of Health Science Research, 1995.
Bernoux, et al., "Estrogen receptor negative and progesterone receptor positive primary breast cancer: pathological characteristics and clinical outcome," Breast Cancer Res Treat, Institut Curie Breast Cancer Study Group, PubMed PMID: 9776505, vol. 49, No. 3, pp. 219-225., 1998.
Boyle, et al., "Influence of cellular location of expressed antigen on the efficacy of DNA vaccination: cytotoxic T lymphocyte and antibody responses are suboptimal when antigen is cytoplasmic after intramuscular DNA immunization," Int Immunol, vol. 9, No. 12, pp. 1897-1906, PubMed PMID: 9466317, 1997.
Breastcancer.org, "Mammography: Benefits, Risks, What You Need to Know," Available from: http://www.breastcancer.org/symptoms/testing/types/mammograms/benefits_risks.jsp. , 2013.
Casiano, et al., "Tumor-associated antigen arrays for the serological diagnosis of cancer," Mol Cell Proteomics, vol. 5, No. 10, pp. 1745-1759. 2006.
Desmetz , "Autoantibody signatures: progress and perspectives for early cancer detection," Journal of cellular and molecular medicine, vol. 15, No. 10, pp. 2013-2024, 2011.
Disis, et al., "High-titer HER-2/neu protein-specific antibody can be detected in patients with early-stage breast cancer," J Clin Oncol, vol. 15, No. 11, pp. 3363-3367, Epub Nov. 18, 1997. PubMed PMID: 9363867, 1997.
Dowsett, et al., "Assessment of HER2 status in breast cancer: why, when and how?" Eur J Cancer, PubMed PMID 10741274 , vol. 36, No. 2, pp. 170-176, 2000.
Drew, et al., "Humoral immune responses to DNA vaccines expressing secreted, membrane bound and non-secreted forms of the Tania ovis 45W antigen," Vaccine, vol. 18, No. 23, pp. 2522-2532. PubMed PMID: 10775786, 2000.
Egland, et al., "Discovery of the breast cancer gene BASE using a molecular approach to enrich for genes encoding membrane and secreted proteins" Proc Natl Acad Sci USA, vol. 100, No. 3, pp. 1099-1104. PubMed PMID: 12538848., 2003.
Ehrlich, et al., "The 'reverse capture' autoantibody microarray: a native antigen-based platform for autoantibody profiling," Nature protocols, vol. 1, No. 1, pp. 452-460, Epub Apr. 5, 2007. doi: 10.1038/nprot.2006.66. PubMed PMID: 17406268, 2006.
Evans, et al. "Classifying patients for breast cancer by detection of autoantibodies against a panel of conformation-carrying antigens," Cancer Prevention Research, vol. 7, No. 5, pp. 545-555, Mar. 2014.
Finn, "Immune response as a biomarker for cancer detection and a lot more," N Engl J Med. vol. 353, No. 12, pp. 1288-1290. PubMed PMID: 16177255, 2005.

(Continued)

*Primary Examiner* — Sean E Aeder
(74) *Attorney, Agent, or Firm* — McDonnell Boehnen Hulbert & Berghoff LLP

(57) ABSTRACT

The present invention provides compositions including reagents for detecting human autoantibodies against at least two proteins selected from the group consisting of ANGTPL4, DKK1, EPHA2, LAMC2, SPON2, SSR2, GAL1, GFRA1, LRRC15, CD147, CD320, CDH3, LRP10, SPINT2, SUSD2, and CST2, and their use in detecting breast cancer or disease recurrence.

21 Claims, 2 Drawing Sheets

(56) References Cited

PUBLICATIONS

Gion, "Comparison of the diagnostic accuracy of CA27.29 and CA15.3 in primary breast cancer," Clin Chem, No. 45, vol. 5, pp. 630-637, Epub May 1, 1999. PubMed PMID: 10222349, 1999.

Hosmer, et al., "Goodness of fit tests for the multiple logistic regression model," Communications in Statistics—Theory and Methods: Taylor & Francis Group, pp. 1043-1069, 1980.

International Search Report for PCT/US2015/021007, dated Sep. 2, 2015.

Kaklamani, "A genetic signature can predict prognosis and response to therapy in breast cancer: Oncotype DX. Expert review of molecular diagnostics," Epub Dec. 5, 2006. doi: 10.1586/14737159.6.6.803. PubMed PMID: 17140367, vol. 6, No. 6, pp. 803-809, 2006.

Kotera, et al., "Humoral immunity against a tandem repeat epitope of human mucin MUC-1 in sera from breast, pancreatic, and colon cancer patients," Cancer Res, vol. 54, No. 11, pp. 2856-2860, Epub Jun. 1, 1994. PubMed PMID: 7514493., 1994.

Krogh, et al., Predicting transmembrane protein topology with a hidden Markov model: application to complete genomes, J Mol Biol, vol. 305, No. 3, pp. 567-580, doi: 10.1006/jmbi.2000.4315. PubMed PMID: 11152613, 2001.

Lacombe, et al., "Identification and validation of new autoantibodies for the diagnosis of DCIS and node negative early-stage breast cancers," Int J Cancer, vol. 132, No. 5, pp. 1105-1113, Epub Aug. 14, 2012. doi: 10.1002/ijc.27766. PubMed PMID: 22886747,2013.

Ladd, et al., "Autoantibody signatures involving glycolysis and splicesome proteins precede a diagnosis of breast cancer among postmenopausal women," Cancer Res, vol. 73, No. 5, pp. 1502-1513, Epub Dec. 28, 2012. doi: 10.1158/0008-5472.CAN-12-2560. PubMed PMID: 23269276, 2013.

Laver, et al., "Epitopes on protein antigens: misconceptions and realities," Cell, vol. 61, No. 4, pp. 553-556, PubMed PMID: 1693095, 1990.

Lu, "Humoral Immunity Directed against Tumor-Associated Antigens as Potential Biomarkers for the Early Diagnosis of Cancer," J Proteome Res, PubMed PMID: 18311901, vol. 7, No. 4, pp. 1388-1394, 2008.

Mange, et al., "Serum autoantibody signature of ductal carcinoma in situ progression to invasive breast cancer," Clin Cancer Res., vol. 18, No. 7, pp. 1992-2000, Epub Feb. 11, 2012. doi: 10.1158/1078-0432.CCR-11-2527. PubMed PMID: 22322670, 2012.

Manjili, et al., "Signatures of tumor-immune interactions as biomarkers for breast cancer prognosis," Future Oncol., PubMed PMID: 22764768, vol. 8, No. 6, pp. 703-711, Epub 2012.

National Cancer Institute at the National Institutes of Health, Available from: http://www.cancer.gov/cancertopics/factsheet/detection/mammograms, 2013.

Neve, et al., "Collection of breast cancer cell lines for the study of functionally distinct cancer subtypes," Cancer Cell, vol. 10, No. 6, pp. 515-527, Epub Dec. 13, 2006. doi: 10.1016/j.ccr.2006.10.008. PubMed PMID: 17157791; PubMed Central PMCID: PMC2730521, 2006.

Nielsen, et al., "Identification of prokaryotic and eukaryotic signal peptides and prediction of their cleavage sites," Protein engineering, No. 10, vol. 1, pp. 1-6, PubMed PMID: 9051728, 1997.

Pavoni, et al., "A study of the humoral immune response of breast cancer patients to a panel of human tumor antigens identified by phage display," Cancer Detect Prev, vol. 30, No. 3, pp. 248-256. PubMed PMID: 16876336, 2006.

Perou, et al., "Molecular portraits of human breast tumours," Nature, vol. 406, No. 6797, pp. 747-752, Epub Aug. 30, 2000. doi: 10.1038/35021093. PubMed PMID: 10963602., 2000.

Piura, Autoantibodies to tailor-made panels of tumor-associated antigens in breast carcinoma, No Journal of oncology, Epub Mar. 23, 2011. doi: 10.1155/2011/982425. PubMed PMID: 21423545; PubMed Central PMCID: PMC3056218., 2011.

Piura, et al., "Autoantibodies to tumor-associated antigens in breast carcinoma," Journal of oncology, Epub Nov. 30, 2010. doi: 10.1155/2010/264926. PubMed PMID: 21113302; PubMed Central PMCID: PMC2989457., 2010.

Ramachandran, et al., "Self-assembling protein microarrays," Science, vol. 305, No. 5680, pp. 86-90, Epub Jul. 3, 2004. doi: 10.1126/science.1097639305/5680/86 [pii]. PubMed PMID: 15232106, 2004.

Reuschenbach, et al., "A systematic review of humoral immune responses against tumor antigens," Cancer immunology, immunotherapy : CII, PubMed PMID: 19562338, vol. 58, No. 10, pp. 1535-1544. Epub 2009.

Shak, "Overview of the trastuzumab (Herceptin) anti-HER2 monoclonal antibody clinical program in HER2-overexpressing metastatic breast cancer. Herceptin Multinational Investigator Study Group," Semin Oncol., PubMed PMID: 10482196, vol. 26, No. 4, Suppl 12, pp. 71-77, 1999.

Sioud, et al., "Profiling the immune response in patients with breast cancer by phage-displayed cDNA libraries," Eur J Immunol, vol. 31, No. 3, pp. 716-725. PubMed PMID: 11241275, 2001.

Slamon, et al., "Human breast cancer: correlation of relapse and survival with amplification of the HER-2/neu oncogene," Science, PubMed PMID: 3798106 , vol. 235, No. 4785, pp. 177-182, 1987.

Slamon, et al., "Studies of the HER-2/neu proto-oncogene in human breast and ovarian cancer," Science, PubMed PMID: 2470152, vol. 244, No. 4905, pp. 707-712, 1989.

Storr, et al., "Use of autoantibodies in breast cancer screening and diagnosis," Expert Rev Anticancer Ther, vol. 6, No. 8, pp. 1215-1223, PubMed PMID: 16925487, 2006.

Tan, "Relative paradigms between autoantibodies in lupus and autoantibodies in cancer," Clin Exp Immunol, vol. 134, No. 2, pp. 169-177, PubMed PMID: 14616773., 2003.

Tan, et al., "Serum autoantibodies as biomarkers for early cancer detection," The FEBS journal, vol. 276, No. 23, pp. 6880-6904, Epub Oct. 29, 2009. doi: 10.1111/j.1742-4658.2009.07396.x. PubMed PMID: 19860826, 2009.

Von Mensdorff-Pouilly, et al., "Humoral immune response to polymorphic epithelial mucin (MUC-1) in patients with benign and malignant breast tumours," Eur J Cancer, vol. 32A, No. 8, pp. 1325-1331, Epub Jul. 1, 1996. PubMed PMID: 8869094., 1996.

Ye H, Sun C, Ren P, Dai L, Peng B, Wang K, et al. Mini-array of multiple tumor-associated antigens (TAAs) in the immunodiagnosis of breast cancer. Oncology letters. 2013;5(2):663-8. Epub Feb. 20, 2013. doi: 10.3892/ol.2012.1062. PubMed PMID: 23420714; PubMed Central PMCID: PMC3573153.

* cited by examiner

SEQUENCE LISTING

```
<160> NUMBER OF SEQ ID NOS: 24

<210> SEQ ID NO 1
<211> LENGTH: 376
<212> TYPE: PRT
<213> ORGANISM: Artificial Sequence
<220> FEATURE:
<223> OTHER INFORMATION: Synthetic

<400> SEQUENCE: 1

Lys Ser Pro Arg Phe Ala Ser Trp Asp Glu Met Asn Val Leu Ala His
1               5                   10                  15

Gly Leu Leu Gln Leu Gly Gln Gly Leu Arg Glu His Ala Glu Arg Thr
            20                  25                  30

Arg Ser Gln Leu Ser Ala Leu Glu Arg Arg Leu Ser Ala Cys Gly Ser
        35                  40                  45

Ala Cys Gln Gly Thr Glu Gly Ser Thr Asp Leu Pro Leu Ala Pro Glu
    50                  55                  60

Ser Arg Val Asp Pro Glu Val Leu His Ser Leu Gln Thr Gln Leu Lys
65                  70                  75                  80

Ala Gln Asn Ser Arg Ile Gln Gln Leu Phe His Lys Val Ala Gln Gln
                85                  90                  95

Gln Arg His Leu Glu Lys Gln His Leu Arg Ile Gln His Leu Gln Ser
            100                 105                 110

Gln Phe Gly Leu Leu Asp His Lys His Leu Asp His Glu Val Ala Lys
        115                 120                 125

Pro Ala Arg Arg Lys Arg Leu Pro Glu Met Ala Gln Pro Val Asp Pro
    130                 135                 140

Ala His Asn Val Ser Arg Leu His Arg Leu Pro Arg Asp Cys Gln Glu
145                 150                 155                 160

Leu Phe Gln Val Gly Glu Arg Gln Ser Gly Leu Phe Glu Ile Gln Pro
                165                 170                 175

Gln Gly Ser Pro Pro Phe Leu Val Asn Cys Lys Met Thr Ser Asp Gly
```

```
            180                 185                 190
Gly Trp Thr Val Ile Gln Arg Arg His Asp Gly Ser Val Asp Phe Asn
            195                 200                 205
Arg Pro Trp Glu Ala Tyr Lys Ala Gly Phe Gly Asp Pro His Gly Glu
            210                 215                 220
Phe Trp Leu Gly Leu Glu Lys Val His Ser Ile Thr Gly Asp Arg Asn
225                 230                 235                 240
Ser Arg Leu Ala Val Gln Leu Arg Asp Trp Asp Gly Asn Ala Glu Leu
            245                 250                 255
Leu Gln Phe Ser Val His Leu Gly Gly Glu Asp Thr Ala Tyr Ser Leu
            260                 265                 270
Gln Leu Thr Ala Pro Val Ala Gly Gln Leu Gly Ala Thr Thr Val Pro
            275                 280                 285
Pro Ser Gly Leu Ser Val Pro Phe Ser Thr Trp Asp Gln Asp His Asp
            290                 295                 300
Leu Arg Arg Asp Lys Asn Cys Ala Lys Ser Leu Ser Gly Gly Trp Trp
305                 310                 315                 320
Phe Gly Thr Cys Ser His Ser Asn Leu Asn Gly Gln Tyr Phe Arg Ser
            325                 330                 335
Ile Pro Gln Gln Arg Gln Lys Leu Lys Lys Gly Ile Phe Trp Lys Thr
            340                 345                 350
Trp Arg Gly Arg Tyr Tyr Pro Leu Gln Ala Thr Thr Met Leu Ile Gln
            355                 360                 365
Pro Met Ala Ala Glu Ala Ala Ser
            370                 375

<210> SEQ ID NO 2
<211> LENGTH: 238
<212> TYPE: PRT
<213> ORGANISM: Artificial Sequence
<220> FEATURE:
<223> OTHER INFORMATION: Synthetic

<400> SEQUENCE: 2

Val Ser Ala Thr Leu Asn Ser Val Leu Asn Ser Asn Ala Ile Lys Asn
1               5                   10                  15
Leu Pro Pro Pro Leu Gly Gly Ala Ala Gly His Pro Gly Ser Ala Val
            20                  25                  30
Ser Ala Ala Pro Gly Ile Leu Tyr Pro Gly Gly Asn Lys Tyr Gln Thr
            35                  40                  45
Ile Asp Asn Tyr Gln Pro Tyr Pro Cys Ala Glu Asp Glu Glu Cys Gly
        50                  55                  60
Thr Asp Glu Tyr Cys Ala Ser Pro Thr Arg Gly Gly Asp Ala Gly Val
65                  70                  75                  80
Gln Ile Cys Leu Ala Cys Arg Lys Arg Lys Arg Cys Met Arg His
            85                  90                  95
Ala Met Cys Cys Pro Gly Asn Tyr Cys Lys Asn Gly Ile Cys Val Ser
            100                 105                 110
Ser Asp Gln Asn His Phe Arg Gly Glu Ile Glu Glu Thr Ile Thr Glu
            115                 120                 125
Ser Phe Gly Asn Asp His Ser Thr Leu Asp Gly Tyr Ser Arg Arg Thr
            130                 135                 140
Thr Leu Ser Ser Lys Met Tyr His Thr Lys Gly Gln Glu Gly Ser Val
145                 150                 155                 160
Cys Leu Arg Ser Ser Asp Cys Ala Ser Gly Leu Cys Cys Ala Arg His
```

```
                    165                 170                 175
Phe Trp Ser Lys Ile Cys Lys Pro Val Leu Lys Glu Gly Gln Val Cys
                180                 185                 190
Thr Lys His Arg Lys Gly Ser His Gly Leu Glu Ile Phe Gln Arg
            195                 200                 205
Cys Tyr Cys Gly Glu Gly Leu Ser Cys Arg Ile Gln Lys Asp His His
            210                 215                 220
Gln Ala Ser Asn Ser Ser Arg Leu His Thr Cys Gln Arg His
225                 230                 235

<210> SEQ ID NO 3
<211> LENGTH: 509
<212> TYPE: PRT
<213> ORGANISM: Artificial Sequence
<220> FEATURE:
<223> OTHER INFORMATION: Synthetic

<400> SEQUENCE: 3

Lys Glu Val Val Leu Leu Asp Phe Ala Ala Gly Gly Glu Leu Gly
1               5                   10                  15
Trp Leu Thr His Pro Tyr Gly Lys Gly Trp Asp Leu Met Gln Asn Ile
            20                  25                  30
Met Asn Asp Met Pro Ile Tyr Met Tyr Ser Val Cys Asn Val Met Ser
        35                  40                  45
Gly Asp Gln Asp Asn Trp Leu Arg Thr Asn Trp Val Tyr Arg Gly Glu
    50                  55                  60
Ala Glu Arg Ile Phe Ile Glu Leu Lys Phe Thr Val Arg Asp Cys Asn
65                  70                  75                  80
Ser Phe Pro Gly Gly Ala Ser Ser Cys Lys Glu Thr Phe Asn Leu Tyr
                85                  90                  95
Tyr Ala Glu Ser Asp Leu Asp Tyr Gly Thr Asn Phe Gln Lys Arg Leu
            100                 105                 110
Phe Thr Lys Ile Asp Thr Ile Ala Pro Asp Glu Ile Thr Val Ser Ser
            115                 120                 125
Asp Phe Glu Ala Arg His Val Lys Leu Asn Val Glu Glu Arg Ser Val
130                 135                 140
Gly Pro Leu Thr Arg Lys Gly Phe Tyr Leu Ala Phe Gln Asp Ile Gly
145                 150                 155                 160
Ala Cys Val Ala Leu Leu Ser Val Arg Val Tyr Tyr Lys Lys Cys Pro
                165                 170                 175
Glu Leu Leu Gln Gly Leu Ala His Phe Pro Glu Thr Ile Ala Gly Ser
            180                 185                 190
Asp Ala Pro Ser Leu Ala Thr Val Ala Gly Thr Cys Val Asp His Ala
            195                 200                 205
Val Val Pro Pro Gly Gly Glu Pro Arg Met His Cys Ala Val Asp
210                 215                 220
Gly Glu Trp Leu Val Pro Ile Gly Gln Cys Leu Cys Gln Ala Gly Tyr
225                 230                 235                 240
Glu Lys Val Glu Asp Ala Cys Gln Ala Cys Ser Pro Gly Phe Lys
            245                 250                 255
Phe Glu Ala Ser Glu Ser Pro Cys Leu Glu Cys Pro Glu His Thr Leu
            260                 265                 270
Pro Ser Pro Glu Gly Ala Thr Ser Cys Glu Cys Glu Glu Gly Phe Phe
            275                 280                 285
Arg Ala Pro Gln Asp Pro Ala Ser Met Pro Cys Thr Arg Pro Pro Ser
```

```
            290                 295                 300
Ala Pro His Tyr Leu Thr Ala Val Gly Met Gly Ala Lys Val Glu Leu
305                 310                 315                 320

Arg Trp Thr Pro Pro Gln Asp Ser Gly Gly Arg Glu Asp Ile Val Tyr
                325                 330                 335

Ser Val Thr Cys Glu Gln Cys Trp Pro Glu Ser Gly Glu Cys Gly Pro
                340                 345                 350

Cys Glu Ala Ser Val Arg Tyr Ser Glu Pro Pro His Gly Leu Thr Arg
            355                 360                 365

Thr Ser Val Thr Val Ser Asp Leu Glu Pro His Met Asn Tyr Thr Phe
        370                 375                 380

Thr Val Glu Ala Arg Asn Gly Val Ser Gly Leu Val Thr Ser Arg Ser
385                 390                 395                 400

Phe Arg Thr Ala Ser Val Ser Ile Asn Gln Thr Glu Pro Pro Lys Val
                405                 410                 415

Arg Leu Glu Gly Arg Ser Thr Thr Ser Leu Ser Val Ser Trp Ser Ile
                420                 425                 430

Pro Pro Pro Gln Gln Ser Arg Val Trp Lys Tyr Glu Val Thr Tyr Arg
                435                 440                 445

Lys Lys Gly Asp Ser Asn Ser Tyr Asn Val Arg Arg Thr Glu Gly Phe
            450                 455                 460

Ser Val Thr Leu Asp Asp Leu Ala Pro Asp Thr Thr Tyr Leu Val Gln
465                 470                 475                 480

Val Gln Ala Leu Thr Gln Glu Gly Gln Gly Ala Gly Ser Lys Val His
                485                 490                 495

Glu Phe Gln Thr Leu Ser Pro Glu Gly Ser Gly Asn Leu
                500                 505

<210> SEQ ID NO 4
<211> LENGTH: 1090
<212> TYPE: PRT
<213> ORGANISM: Artificial Sequence
<220> FEATURE:
<223> OTHER INFORMATION: Synthetic

<400> SEQUENCE: 4

Thr Ser Arg Arg Glu Val Cys Asp Cys Asn Gly Lys Ser Arg Gln Cys
1               5                   10                  15

Ile Phe Asp Arg Glu Leu His Arg Gln Thr Gly Asn Gly Phe Arg Cys
                20                  25                  30

Leu Asn Cys Asn Asp Asn Thr Asp Gly Ile His Cys Glu Lys Cys Lys
            35                  40                  45

Asn Gly Phe Tyr Arg His Arg Glu Arg Asp Arg Cys Leu Pro Cys Asn
        50                  55                  60

Cys Asn Ser Lys Gly Ser Leu Ser Ala Arg Cys Asp Asn Ser Gly Arg
65                  70                  75                  80

Cys Ser Cys Lys Pro Gly Val Thr Gly Ala Arg Cys Asp Arg Cys Leu
                85                  90                  95

Pro Gly Phe His Met Leu Thr Asp Ala Gly Cys Thr Gln Asp Gln Arg
                100                 105                 110

Leu Leu Asp Ser Lys Cys Asp Cys Asp Pro Ala Gly Ile Ala Gly Pro
            115                 120                 125

Cys Asp Ala Gly Arg Cys Val Cys Lys Pro Ala Val Thr Gly Glu Arg
        130                 135                 140

Cys Asp Arg Cys Arg Ser Gly Tyr Tyr Asn Leu Asp Gly Gly Asn Pro
```

-continued

```
        145                 150                 155                 160
    Glu Gly Cys Thr Gln Cys Phe Cys Tyr Gly His Ser Ala Ser Cys Arg
                        165                 170                 175
    Ser Ser Ala Glu Tyr Ser Val His Lys Ile Thr Ser Thr Phe His Gln
                        180                 185                 190
    Asp Val Asp Gly Trp Lys Ala Val Gln Arg Asn Gly Ser Pro Ala Lys
                        195                 200                 205
    Leu Gln Trp Ser Gln Arg His Gln Asp Val Phe Ser Ser Ala Gln Arg
                        210                 215                 220
    Leu Asp Pro Val Tyr Phe Val Ala Pro Ala Lys Phe Leu Gly Asn Gln
    225                 230                 235                 240
    Gln Val Ser Tyr Gly Gln Ser Leu Ser Phe Asp Tyr Arg Val Asp Arg
                        245                 250                 255
    Gly Gly Arg His Pro Ser Ala His Asp Val Ile Leu Glu Gly Ala Gly
                        260                 265                 270
    Leu Arg Ile Thr Ala Pro Leu Met Pro Leu Gly Lys Thr Leu Pro Cys
                        275                 280                 285
    Gly Leu Thr Lys Thr Tyr Thr Phe Arg Leu Asn Glu His Pro Ser Asn
                        290                 295                 300
    Asn Trp Ser Pro Gln Leu Ser Tyr Phe Glu Tyr Arg Arg Leu Leu Arg
    305                 310                 315                 320
    Asn Leu Thr Ala Leu Arg Ile Arg Ala Thr Tyr Gly Glu Tyr Ser Thr
                        325                 330                 335
    Gly Tyr Ile Asp Asn Val Thr Leu Ile Ser Ala Arg Pro Val Ser Gly
                        340                 345                 350
    Ala Pro Ala Pro Trp Val Glu Gln Cys Ile Cys Pro Val Gly Tyr Lys
                        355                 360                 365
    Gly Gln Phe Cys Gln Asp Cys Ala Ser Gly Tyr Lys Arg Asp Ser Ala
                        370                 375                 380
    Arg Leu Gly Pro Phe Gly Thr Cys Ile Pro Cys Asn Cys Gln Gly Gly
    385                 390                 395                 400
    Gly Ala Cys Asp Pro Asp Thr Gly Asp Cys Tyr Ser Gly Asp Glu Asn
                        405                 410                 415
    Pro Asp Ile Glu Cys Ala Asp Cys Pro Ile Gly Phe Tyr Asn Asp Pro
                        420                 425                 430
    His Asp Pro Arg Ser Cys Lys Pro Cys Pro Cys His Asn Gly Phe Ser
                        435                 440                 445
    Cys Ser Val Met Pro Glu Thr Glu Glu Val Val Cys Asn Asn Cys Pro
                        450                 455                 460
    Pro Gly Val Thr Gly Ala Arg Cys Glu Leu Cys Ala Asp Gly Tyr Phe
    465                 470                 475                 480
    Gly Asp Pro Phe Gly Glu His Gly Pro Val Arg Pro Cys Gln Pro Cys
                        485                 490                 495
    Gln Cys Asn Asn Asn Val Asp Pro Ser Ala Ser Gly Asn Cys Asp Arg
                        500                 505                 510
    Leu Thr Gly Arg Cys Leu Lys Cys Ile His Asn Thr Ala Gly Ile Tyr
                        515                 520                 525
    Cys Asp Gln Cys Lys Ala Gly Tyr Phe Gly Asp Pro Leu Ala Pro Asn
                        530                 535                 540
    Pro Ala Asp Lys Cys Arg Ala Cys Asn Cys Asn Pro Met Gly Ser Glu
    545                 550                 555                 560
    Pro Val Gly Cys Arg Ser Asp Gly Thr Cys Val Cys Lys Pro Gly Phe
                        565                 570                 575
```

-continued

```
Gly Gly Pro Asn Cys Glu His Gly Ala Phe Ser Cys Pro Ala Cys Tyr
            580                 585                 590
Asn Gln Val Lys Ile Gln Met Asp Gln Phe Met Gln Leu Gln Arg
        595                 600                 605
Met Glu Ala Leu Ile Ser Lys Ala Gln Gly Gly Asp Gly Val Val Pro
610                 615                 620
Asp Thr Glu Leu Glu Gly Arg Met Gln Ala Glu Gln Ala Leu Gln
625                 630                 635                 640
Asp Ile Leu Arg Asp Ala Gln Ile Ser Glu Gly Ala Ser Arg Ser Leu
                645                 650                 655
Gly Leu Gln Leu Ala Lys Val Arg Ser Gln Glu Asn Ser Tyr Gln Ser
            660                 665                 670
Arg Leu Asp Asp Leu Lys Met Thr Val Glu Arg Val Arg Ala Leu Gly
        675                 680                 685
Ser Gln Tyr Gln Asn Arg Val Arg Asp Thr His Arg Leu Ile Thr Gln
            690                 695                 700
Met Gln Leu Ser Leu Ala Glu Ser Glu Ala Ser Leu Gly Asn Thr Asn
705                 710                 715                 720
Ile Pro Ala Ser Asp His Tyr Val Gly Pro Asn Gly Phe Lys Ser Leu
                725                 730                 735
Ala Gln Glu Ala Thr Arg Leu Ala Glu Ser His Val Glu Ser Ala Ser
            740                 745                 750
Asn Met Glu Gln Leu Thr Arg Glu Thr Glu Asp Tyr Ser Lys Gln Ala
        755                 760                 765
Leu Ser Leu Val Arg Lys Ala Leu His Glu Gly Val Gly Ser Gly Ser
770                 775                 780
Gly Ser Pro Asp Gly Ala Val Val Gln Gly Leu Val Glu Lys Leu Glu
785                 790                 795                 800
Lys Thr Lys Ser Leu Ala Gln Gln Leu Thr Arg Glu Ala Thr Gln Ala
                805                 810                 815
Glu Ile Glu Ala Asp Arg Ser Tyr Gln His Ser Leu Arg Leu Leu Asp
            820                 825                 830
Ser Val Ser Arg Leu Gln Gly Val Ser Asp Gln Ser Phe Gln Val Glu
        835                 840                 845
Glu Ala Lys Arg Ile Lys Gln Lys Ala Asp Ser Leu Ser Ser Leu Val
        850                 855                 860
Thr Arg His Met Asp Glu Phe Lys Arg Thr Gln Lys Asn Leu Gly Asn
865                 870                 875                 880
Trp Lys Glu Glu Ala Gln Gln Leu Leu Gln Asn Gly Lys Ser Gly Arg
                885                 890                 895
Glu Lys Ser Asp Gln Leu Leu Ser Arg Ala Asn Leu Ala Lys Ser Arg
            900                 905                 910
Ala Gln Glu Ala Leu Ser Met Gly Asn Ala Thr Phe Tyr Glu Val Glu
            915                 920                 925
Ser Ile Leu Lys Asn Leu Arg Glu Phe Asp Leu Gln Val Asp Asn Arg
        930                 935                 940
Lys Ala Glu Ala Glu Ala Met Lys Arg Leu Ser Tyr Ile Ser Gln
945                 950                 955                 960
Lys Val Ser Asp Ala Ser Asp Lys Thr Gln Gln Ala Glu Arg Ala Leu
                965                 970                 975
Gly Ser Ala Ala Ala Asp Ala Gln Arg Ala Lys Asn Gly Ala Gly Glu
            980                 985                 990
```

```
Ala Leu Glu Ile Ser Ser Glu Ile Glu Gln Glu Ile Gly  Ser Leu Asn
         995                 1000                1005

Leu Glu  Ala Asn Val Thr Ala  Asp Gly Ala Leu Ala  Met Glu Lys
    1010                 1015                1020

Gly Leu  Ala Ser Leu Lys Ser  Glu Met Arg Glu Val  Glu Gly Glu
    1025                 1030                1035

Leu Glu  Arg Lys Glu Leu Glu  Phe Asp Thr Asn Met  Asp Ala Val
    1040                 1045                1050

Gln Met  Val Ile Thr Glu Ala  Gln Lys Val Asp Thr  Arg Ala Lys
    1055                 1060                1065

Asn Ala  Gly Val Thr Ile Gln  Asp Thr Leu Asn Thr  Leu Asp Gly
    1070                 1075                1080

Leu Leu  His Leu Met Gly Met
    1085                 1090

<210> SEQ ID NO 5
<211> LENGTH: 305
<212> TYPE: PRT
<213> ORGANISM: Artificial Sequence
<220> FEATURE:
<223> OTHER INFORMATION: Synthetic

<400> SEQUENCE: 5

Gln Pro Leu Gly Gly Glu Ser Ile Cys Ser Ala Arg Ala Pro Ala Lys
1               5                   10                  15

Tyr Ser Ile Thr Phe Thr Gly Lys Trp Ser Gln Thr Ala Phe Pro Lys
            20                  25                  30

Gln Tyr Pro Leu Phe Arg Pro Pro Ala Gln Trp Ser Ser Leu Leu Gly
        35                  40                  45

Ala Ala His Ser Ser Asp Tyr Ser Met Trp Arg Lys Asn Gln Tyr Val
    50                  55                  60

Ser Asn Gly Leu Arg Asp Phe Ala Glu Arg Gly Glu Ala Trp Ala Leu
65                  70                  75                  80

Met Lys Glu Ile Glu Ala Ala Gly Glu Ala Leu Gln Ser Val His Glu
                85                  90                  95

Val Phe Ser Ala Pro Ala Val Pro Ser Gly Thr Gly Gln Thr Ser Ala
            100                 105                 110

Glu Leu Glu Val Gln Arg Arg His Ser Leu Val Ser Phe Val Val Arg
        115                 120                 125

Ile Val Pro Ser Pro Asp Trp Phe Val Gly Val Asp Ser Leu Asp Leu
    130                 135                 140

Cys Asp Gly Asp Arg Trp Arg Glu Gln Ala Ala Leu Asp Leu Tyr Pro
145                 150                 155                 160

Tyr Asp Ala Gly Thr Asp Ser Gly Phe Thr Phe Ser Ser Pro Asn Phe
                165                 170                 175

Ala Thr Ile Pro Gln Asp Thr Val Thr Glu Ile Thr Ser Ser Ser Pro
            180                 185                 190

Ser His Pro Ala Asn Ser Phe Tyr Tyr Pro Arg Leu Lys Ala Leu Pro
        195                 200                 205

Pro Ile Ala Arg Val Thr Leu Leu Arg Leu Arg Gln Ser Pro Arg Ala
    210                 215                 220

Phe Ile Pro Pro Ala Pro Val Leu Pro Ser Arg Asp Asn Glu Ile Val
225                 230                 235                 240

Asp Ser Ala Ser Val Pro Glu Thr Pro Leu Asp Cys Glu Val Ser Leu
                245                 250                 255
```

```
Trp Ser Ser Trp Gly Leu Cys Gly Gly His Cys Gly Arg Leu Gly Thr
            260                 265                 270

Lys Ser Arg Thr Arg Tyr Val Arg Val Gln Pro Ala Asn Asn Gly Ser
        275                 280                 285

Pro Cys Pro Glu Leu Glu Glu Ala Glu Cys Val Pro Asp Asn Cys
    290                 295                 300

Val
305

<210> SEQ ID NO 6
<211> LENGTH: 129
<212> TYPE: PRT
<213> ORGANISM: Artificial Sequence
<220> FEATURE:
<223> OTHER INFORMATION: Synthetic

<400> SEQUENCE: 6

Glu Glu Gly Ala Arg Leu Leu Ala Ser Lys Ser Leu Leu Asn Arg Tyr
1               5                   10                  15

Ala Val Glu Gly Arg Asp Leu Thr Leu Gln Tyr Asn Ile Tyr Asn Val
            20                  25                  30

Gly Ser Ser Ala Ala Leu Asp Val Glu Leu Ser Asp Ser Phe Pro
        35                  40                  45

Pro Glu Asp Phe Gly Ile Val Ser Gly Met Leu Asn Val Lys Trp Asp
    50                  55                  60

Arg Ile Ala Pro Ala Ser Asn Val Ser His Thr Val Val Leu Arg Pro
65                  70                  75                  80

Leu Lys Ala Gly Tyr Phe Asn Phe Thr Ser Ala Thr Ile Thr Tyr Leu
                85                  90                  95

Ala Gln Glu Asp Gly Pro Val Val Ile Gly Ser Thr Ser Ala Pro Gly
            100                 105                 110

Gln Gly Gly Ile Leu Ala Gln Arg Glu Phe Asp Arg Arg Phe Ser Pro
        115                 120                 125

His

<210> SEQ ID NO 7
<211> LENGTH: 118
<212> TYPE: PRT
<213> ORGANISM: Artificial Sequence
<220> FEATURE:
<223> OTHER INFORMATION: Synthetic

<400> SEQUENCE: 7

Leu Arg Val Arg Gly Glu Val Ala Pro Asp Ala Lys Ser Phe Val Leu
1               5                   10                  15

Asn Leu Gly Lys Asp Ser Asn Asn Leu Cys Leu His Phe Asn Pro Arg
            20                  25                  30

Phe Asn Ala His Gly Asp Ala Asn Thr Ile Val Cys Asn Ser Lys Asp
        35                  40                  45

Gly Gly Ala Trp Gly Thr Glu Gln Arg Glu Ala Val Phe Pro Phe Gln
    50                  55                  60

Pro Gly Ser Val Ala Glu Val Cys Ile Thr Phe Asp Gln Ala Asn Leu
65                  70                  75                  80

Thr Val Lys Leu Pro Asp Gly Tyr Glu Phe Lys Phe Pro Asn Arg Leu
                85                  90                  95

Asn Leu Glu Ala Ile Asn Tyr Met Ala Ala Asp Gly Asp Phe Lys Ile
            100                 105                 110
```

```
Lys Cys Val Ala Phe Asp
        115

<210> SEQ ID NO 8
<211> LENGTH: 441
<212> TYPE: PRT
<213> ORGANISM: Artificial Sequence
<220> FEATURE:
<223> OTHER INFORMATION: Synthetic

<400> SEQUENCE: 8

Asp Arg Leu Asp Cys Val Lys Ala Ser Asp Gln Cys Leu Lys Glu Gln
1               5                   10                  15

Ser Cys Ser Thr Lys Tyr Arg Thr Leu Arg Gln Cys Val Ala Gly Lys
            20                  25                  30

Glu Thr Asn Phe Ser Leu Ala Ser Gly Leu Glu Ala Lys Asp Glu Cys
        35                  40                  45

Arg Ser Ala Met Glu Ala Leu Lys Gln Lys Ser Leu Tyr Asn Cys Arg
    50                  55                  60

Cys Lys Arg Gly Met Lys Lys Glu Lys Asn Cys Leu Arg Ile Tyr Trp
65                  70                  75                  80

Ser Met Tyr Gln Ser Leu Gln Gly Asn Asp Leu Leu Glu Asp Ser Pro
                85                  90                  95

Tyr Glu Pro Val Asn Ser Arg Leu Ser Asp Ile Phe Arg Val Val Pro
            100                 105                 110

Phe Ile Ser Asp Val Phe Gln Gln Val Glu His Ile Pro Lys Gly Asn
        115                 120                 125

Asn Cys Leu Asp Ala Ala Lys Ala Cys Asn Leu Asp Asp Ile Cys Lys
    130                 135                 140

Lys Tyr Arg Ser Ala Tyr Ile Thr Pro Cys Thr Thr Ser Val Ser Asn
145                 150                 155                 160

Asp Val Cys Asn Arg Arg Lys Cys His Lys Ala Leu Arg Gln Phe Phe
                165                 170                 175

Asp Lys Val Pro Ala Lys His Ser Tyr Gly Met Leu Phe Cys Ser Cys
            180                 185                 190

Arg Asp Ile Ala Cys Thr Glu Arg Arg Arg Gln Thr Ile Val Pro Val
        195                 200                 205

Cys Ser Tyr Glu Glu Arg Glu Lys Pro Asn Cys Leu Asn Leu Gln Asp
    210                 215                 220

Ser Cys Lys Thr Asn Tyr Ile Cys Arg Ser Arg Leu Ala Asp Phe Phe
225                 230                 235                 240

Thr Asn Cys Gln Pro Glu Ser Arg Ser Val Ser Ser Cys Leu Lys Glu
                245                 250                 255

Asn Tyr Ala Asp Cys Leu Leu Ala Tyr Ser Gly Leu Ile Gly Thr Val
            260                 265                 270

Met Thr Pro Asn Tyr Ile Asp Ser Ser Leu Ser Val Ala Pro Trp
        275                 280                 285

Cys Asp Cys Ser Asn Ser Gly Asn Asp Leu Glu Glu Cys Leu Lys Phe
    290                 295                 300

Leu Asn Phe Phe Lys Asp Asn Thr Cys Leu Lys Asn Ala Ile Gln Ala
305                 310                 315                 320

Phe Gly Asn Gly Ser Asp Val Thr Val Trp Gln Pro Ala Phe Pro Val
                325                 330                 335

Gln Thr Thr Thr Ala Thr Thr Thr Ala Leu Arg Val Lys Asn Lys
            340                 345                 350
```

```
Pro Leu Gly Pro Ala Gly Ser Glu Asn Glu Ile Pro Thr His Val Leu
            355                 360                 365

Pro Pro Cys Ala Asn Leu Gln Ala Gln Lys Leu Lys Ser Asn Val Ser
370                 375                 380

Gly Asn Thr His Leu Cys Ile Ser Asn Gly Asn Tyr Glu Lys Glu Gly
385                 390                 395                 400

Leu Gly Ala Ser Ser His Ile Thr Thr Lys Ser Met Ala Ala Pro Pro
                405                 410                 415

Ser Cys Gly Leu Ser Pro Leu Leu Val Leu Val Thr Ala Leu Ser
                420                 425                 430

Thr Leu Leu Ser Leu Thr Glu Thr Ser
            435                 440

<210> SEQ ID NO 9
<211> LENGTH: 517
<212> TYPE: PRT
<213> ORGANISM: Artificial Sequence
<220> FEATURE:
<223> OTHER INFORMATION: Synthetic

<400> SEQUENCE: 9

Tyr His Gly Cys Pro Ser Glu Cys Thr Cys Ser Arg Ala Ser Gln Val
1               5                   10                  15

Glu Cys Thr Gly Ala Arg Ile Val Ala Val Pro Thr Pro Leu Pro Trp
            20                  25                  30

Asn Ala Met Ser Leu Gln Ile Leu Asn Thr His Ile Thr Glu Leu Asn
        35                  40                  45

Glu Ser Pro Phe Leu Asn Ile Ser Ala Leu Ile Ala Leu Arg Ile Glu
    50                  55                  60

Lys Asn Glu Leu Ser Arg Ile Thr Pro Gly Ala Phe Arg Asn Leu Gly
65                  70                  75                  80

Ser Leu Arg Tyr Leu Ser Leu Ala Asn Asn Lys Leu Gln Val Leu Pro
                85                  90                  95

Ile Gly Leu Phe Gln Gly Leu Asp Ser Leu Glu Ser Leu Leu Leu Ser
            100                 105                 110

Ser Asn Gln Leu Leu Gln Ile Gln Pro Ala His Phe Ser Gln Cys Ser
        115                 120                 125

Asn Leu Lys Glu Leu Gln Leu His Gly Asn His Leu Glu Tyr Ile Pro
    130                 135                 140

Asp Gly Ala Phe Asp His Leu Val Gly Leu Thr Lys Leu Asn Leu Gly
145                 150                 155                 160

Lys Asn Ser Leu Thr His Ile Ser Pro Arg Val Phe Gln His Leu Gly
                165                 170                 175

Asn Leu Gln Val Leu Arg Leu Tyr Glu Asn Arg Leu Thr Asp Ile Pro
            180                 185                 190

Met Gly Thr Phe Asp Gly Leu Val Asn Leu Gln Glu Leu Ala Leu Gln
        195                 200                 205

Gln Asn Gln Ile Gly Leu Leu Ser Pro Gly Leu Phe His Asn Asn His
    210                 215                 220

Asn Leu Gln Arg Leu Tyr Leu Ser Asn Asn His Ile Ser Gln Leu Pro
225                 230                 235                 240

Pro Ser Val Phe Met Gln Leu Pro Gln Leu Asn Arg Leu Thr Leu Phe
                245                 250                 255

Gly Asn Ser Leu Lys Glu Leu Ser Pro Gly Ile Phe Gly Pro Met Pro
            260                 265                 270
```

Asn Leu Arg Glu Leu Trp Leu Tyr Asp Asn His Ile Ser Ser Leu Pro
            275                 280                 285

Asp Asn Val Phe Ser Asn Leu Arg Gln Leu Gln Val Leu Ile Leu Ser
290                 295                 300

Arg Asn Gln Ile Ser Phe Ile Ser Pro Gly Ala Phe Asn Gly Leu Thr
305                 310                 315                 320

Glu Leu Arg Glu Leu Ser Leu His Thr Asn Ala Leu Gln Asp Leu Asp
            325                 330                 335

Gly Asn Val Phe Arg Met Leu Ala Leu Gln Asn Ile Ser Leu Gln
            340                 345                 350

Asn Asn Arg Leu Arg Gln Leu Pro Gly Asn Ile Phe Ala Asn Val Asn
            355                 360                 365

Gly Leu Met Ala Ile Gln Leu Gln Asn Asn Gln Leu Glu Asn Leu Pro
370                 375                 380

Leu Gly Ile Phe Asp His Leu Gly Lys Leu Cys Glu Leu Arg Leu Tyr
385                 390                 395                 400

Asp Asn Pro Trp Arg Cys Asp Ser Asp Ile Leu Pro Leu Arg Asn Trp
            405                 410                 415

Leu Leu Leu Asn Gln Pro Arg Leu Gly Thr Asp Thr Val Pro Val Cys
            420                 425                 430

Phe Ser Pro Ala Asn Val Arg Gly Gln Ser Leu Ile Ile Ile Asn Val
435                 440                 445

Asn Val Ala Val Pro Ser Val His Val Pro Glu Val Pro Ser Tyr Pro
            450                 455                 460

Glu Thr Pro Trp Tyr Pro Asp Thr Pro Ser Tyr Pro Asp Thr Thr Ser
465                 470                 475                 480

Val Ser Ser Thr Thr Glu Leu Thr Ser Pro Val Glu Asp Tyr Thr Asp
            485                 490                 495

Leu Thr Thr Ile Gln Val Thr Asp Asp Arg Ser Val Trp Gly Met Thr
            500                 505                 510

Gln Ala Gln Ser Gly
            515

<210> SEQ ID NO 10
<211> LENGTH: 576
<212> TYPE: PRT
<213> ORGANISM: Artificial Sequence
<220> FEATURE:
<223> OTHER INFORMATION: Synthetic

<400> SEQUENCE: 10

Thr Arg Cys Pro Asp Gly Gln Phe Cys Pro Val Ala Cys Cys Leu Asp
1               5                   10                  15

Pro Gly Gly Ala Ser Tyr Ser Cys Cys Arg Pro Leu Leu Asp Lys Trp
            20                  25                  30

Pro Thr Thr Leu Ser Arg His Leu Gly Gly Pro Cys Gln Val Asp Ala
            35                  40                  45

His Cys Ser Ala Gly His Ser Cys Ile Phe Thr Val Ser Gly Thr Ser
        50                  55                  60

Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

```
Gln Phe Glu Cys Pro Asp Phe Ser Thr Cys Cys Val Met Val Asp Gly
            115                 120                 125

Ser Trp Gly Cys Cys Pro Met Pro Gln Ala Ser Cys Cys Glu Asp Arg
        130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
```

```
                   530                 535                 540
Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Leu Leu
                565                 570                 575

<210> SEQ ID NO 11
<211> LENGTH: 145
<212> TYPE: PRT
<213> ORGANISM: Artificial Sequence
<220> FEATURE:
<223> OTHER INFORMATION: Synthetic

<400> SEQUENCE: 11

Ala Pro Lys Pro Ala Thr Val Val Thr Gly Ser Gly His Ala Ser Ser
1               5                   10                  15

Thr Pro Gly Gly Glu Lys Glu Thr Ser Ala Thr Gln Arg Ser Ser Val
                20                  25                  30

Pro Ser Ser Thr Glu Lys Asn Ala Phe Asn Ser Ser Leu Glu Asp Pro
            35                  40                  45

Ser Thr Asp Tyr Tyr Gln Glu Leu Gln Arg Asp Ile Ser Glu Met Phe
        50                  55                  60

Leu Gln Ile Tyr Lys Gln Gly Gly Phe Leu Gly Leu Ser Asn Ile Lys
65                  70                  75                  80

Phe Arg Pro Gly Ser Val Val Val Gln Leu Thr Leu Ala Phe Arg Glu
                85                  90                  95

Gly Thr Ile Asn Val His Asp Val Glu Thr Gln Phe Asn Gln Tyr Lys
            100                 105                 110

Thr Glu Ala Ala Ser Arg Tyr Asn Leu Thr Ile Ser Asp Val Ser Val
        115                 120                 125

Ser Asp Val Pro Phe Pro Phe Ser Ala Gln Ser Gly Ala Gly Val Pro
    130                 135                 140

Gly
145

<210> SEQ ID NO 12
<211> LENGTH: 141
<212> TYPE: PRT
<213> ORGANISM: Artificial Sequence
<220> FEATURE:
<223> OTHER INFORMATION: Synthetic

<400> SEQUENCE: 12

Ala Ala Gly Thr Val Phe Thr Thr Val Glu Asp Leu Gly Ser Lys Ile
1               5                   10                  15

Leu Leu Thr Cys Ser Leu Asn Asp Ser Ala Thr Glu Val Thr Gly His
                20                  25                  30

Arg Trp Leu Lys Gly Gly Val Val Leu Lys Glu Asp Ala Leu Pro Gly
            35                  40                  45

Gln Lys Thr Glu Phe Lys Val Asp Ser Asp Asp Gln Trp Gly Glu Tyr
        50                  55                  60

Ser Cys Val Phe Leu Pro Glu Pro Met Gly Thr Ala Asn Ile Gln Leu
65                  70                  75                  80

His Gly Pro Pro Arg Val Lys Ala Val Lys Ser Ser Glu His Ile Asn
                85                  90                  95

Glu Gly Glu Thr Ala Met Leu Val Cys Lys Ser Glu Ser Val Pro Pro
            100                 105                 110
```

```
Val Thr Asp Trp Ala Trp Tyr Lys Ile Thr Asp Ser Glu Asp Lys Ala
            115                 120                 125

Leu Met Asn Gly Ser Glu Ser Arg Phe Phe Val Ser Ser
    130                 135                 140

<210> SEQ ID NO 13
<211> LENGTH: 184
<212> TYPE: PRT
<213> ORGANISM: Artificial Sequence
<220> FEATURE:
<223> OTHER INFORMATION: Synthetic

<400> SEQUENCE: 13

Ala Gly Pro Ser Ser Gly Ser Cys Pro Pro Thr Lys Phe Gln Cys Arg
1               5                   10                  15

Thr Ser Gly Leu Cys Val Pro Leu Thr Trp Arg Cys Asp Arg Asp Leu
            20                  25                  30

Asp Cys Ser Asp Gly Ser Asp Glu Glu Cys Arg Ile Glu Pro Cys
        35                  40                  45

Thr Gln Lys Gly Gln Cys Pro Pro Pro Gly Leu Pro Cys Pro Cys
50                  55                  60

Thr Gly Val Ser Asp Cys Ser Gly Gly Thr Asp Lys Lys Leu Arg Asn
65                  70                  75                  80

Cys Ser Arg Leu Ala Cys Leu Ala Gly Glu Leu Arg Cys Thr Leu Ser
                85                  90                  95

Asp Asp Cys Ile Pro Leu Thr Trp Arg Cys Asp Gly His Pro Asp Cys
            100                 105                 110

Pro Asp Ser Ser Asp Glu Leu Gly Cys Gly Thr Asn Glu Ile Leu Pro
            115                 120                 125

Glu Gly Asp Ala Thr Thr Met Gly Pro Pro Val Thr Leu Glu Ser Val
    130                 135                 140

Thr Ser Leu Arg Asn Ala Thr Thr Met Gly Pro Pro Val Thr Leu Glu
145                 150                 155                 160

Ser Val Pro Ser Val Gly Asn Ala Thr Ser Ser Ala Gly Asp Gln
                165                 170                 175

Ser Gly Ser Pro Thr Ala Tyr Gly
            180

<210> SEQ ID NO 14
<211> LENGTH: 630
<212> TYPE: PRT
<213> ORGANISM: Artificial Sequence
<220> FEATURE:
<223> OTHER INFORMATION: Synthetic

<400> SEQUENCE: 14

Glu Pro Cys Arg Ala Val Phe Arg Glu Ala Glu Val Thr Leu Glu Ala
1               5                   10                  15

Gly Gly Ala Glu Gln Glu Pro Gly Gln Ala Leu Gly Lys Val Phe Met
            20                  25                  30

Gly Cys Pro Gly Gln Glu Pro Ala Leu Phe Ser Thr Asp Asn Asp Asp
        35                  40                  45

Phe Thr Val Arg Asn Gly Glu Thr Val Gln Glu Arg Arg Ser Leu Lys
    50                  55                  60

Glu Arg Asn Pro Leu Lys Ile Phe Pro Ser Lys Ile Leu Arg Arg
65                  70                  75                  80

His Lys Arg Asp Trp Val Val Ala Pro Ile Ser Val Pro Glu Asn Gly
                85                  90                  95
```

-continued

```
Lys Gly Pro Phe Pro Gln Arg Leu Asn Gln Leu Lys Ser Asn Lys Asp
            100                 105                 110

Arg Asp Thr Lys Ile Phe Tyr Ser Ile Thr Gly Pro Gly Ala Asp Ser
        115                 120                 125

Pro Pro Glu Gly Val Phe Ala Val Glu Lys Thr Gly Trp Leu Leu
    130                 135                 140

Leu Asn Lys Pro Leu Asp Arg Glu Glu Ile Ala Lys Tyr Glu Leu Phe
145                 150                 155                 160

Gly His Ala Val Ser Glu Asn Gly Ala Ser Val Asp Pro Met Asn
                165                 170                 175

Ile Ser Ile Ile Val Thr Asp Gln Asn Asp His Lys Pro Lys Phe Thr
            180                 185                 190

Gln Asp Thr Phe Arg Gly Ser Val Leu Glu Gly Val Leu Pro Gly Thr
        195                 200                 205

Ser Val Met Gln Met Thr Ala Thr Asp Glu Asp Asp Ala Ile Tyr Thr
    210                 215                 220

Tyr Asn Gly Val Val Ala Tyr Ser Ile His Ser Gln Glu Pro Lys Asp
225                 230                 235                 240

Pro His Asp Leu Met Phe Thr Ile His Arg Ser Thr Gly Thr Ile Ser
                245                 250                 255

Val Ile Ser Ser Gly Leu Asp Arg Glu Lys Val Pro Glu Tyr Thr Leu
            260                 265                 270

Thr Ile Gln Ala Thr Asp Met Asp Gly Asp Gly Ser Thr Thr Thr Ala
        275                 280                 285

Val Ala Val Val Glu Ile Leu Asp Ala Asn Asp Asn Ala Pro Met Phe
    290                 295                 300

Asp Pro Gln Lys Tyr Glu Ala His Val Pro Glu Asn Ala Val Gly His
305                 310                 315                 320

Glu Val Gln Arg Leu Thr Val Thr Asp Leu Asp Ala Pro Asn Ser Pro
                325                 330                 335

Ala Trp Arg Ala Thr Tyr Leu Ile Met Gly Gly Asp Asp Gly Asp His
            340                 345                 350

Phe Thr Ile Thr Thr His Pro Glu Ser Asn Gln Gly Ile Leu Thr Thr
        355                 360                 365

Arg Lys Gly Leu Asp Phe Glu Ala Lys Asn Gln His Thr Leu Tyr Val
370                 375                 380

Glu Val Thr Asn Glu Ala Pro Phe Val Leu Lys Leu Pro Thr Ser Thr
385                 390                 395                 400

Ala Thr Ile Val Val His Val Glu Asp Val Asn Glu Ala Pro Val Phe
            405                 410                 415

Val Pro Pro Ser Lys Val Val Gln Glu Gly Ile Pro Thr Gly
        420                 425                 430

Glu Pro Val Cys Val Tyr Thr Ala Glu Asp Pro Asp Lys Glu Asn Gln
    435                 440                 445

Lys Ile Ser Tyr Arg Ile Leu Arg Asp Pro Ala Gly Trp Leu Ala Met
        450                 455                 460

Asp Pro Asp Ser Gly Gln Val Thr Ala Val Gly Thr Leu Asp Arg Glu
465                 470                 475                 480

Asp Glu Gln Phe Val Arg Asn Asn Ile Tyr Glu Val Met Val Leu Ala
                485                 490                 495

Met Asp Asn Gly Ser Pro Pro Thr Thr Gly Thr Gly Thr Leu Leu Leu
            500                 505                 510
```

Thr Leu Ile Asp Val Asn Asp His Gly Pro Val Pro Glu Pro Arg Gln
            515                 520                 525

Ile Thr Ile Cys Asn Gln Ser Pro Val Arg Gln Val Leu Asn Ile Thr
        530                 535                 540

Asp Lys Asp Leu Ser Pro His Thr Ser Pro Phe Gln Ala Gln Leu Thr
545                 550                 555                 560

Asp Asp Ser Asp Ile Tyr Trp Thr Ala Glu Val Asn Glu Glu Gly Asp
                565                 570                 575

Thr Val Val Leu Ser Leu Lys Lys Phe Leu Lys Gln Asp Thr Tyr Asp
            580                 585                 590

Val His Leu Ser Leu Ser Asp His Gly Asn Lys Glu Gln Leu Thr Val
        595                 600                 605

Ile Arg Ala Thr Val Cys Asp Cys His Gly His Val Glu Thr Cys Pro
610                 615                 620

Gly Pro Trp Lys Gly Gly
625                 630

<210> SEQ ID NO 15
<211> LENGTH: 630
<212> TYPE: PRT
<213> ORGANISM: Artificial Sequence
<220> FEATURE:
<223> OTHER INFORMATION: Synthetic

<400> SEQUENCE: 15

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
            35                  40                  45

Leu Ser Phe Leu Gln Asp Ile Gln Glu Val Gln Gly Tyr Val Leu Ile
        50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
    610                 615                 620

Arg Ala Ser Pro Leu Thr
625                 630

<210> SEQ ID NO 16
<211> LENGTH: 289
<212> TYPE: PRT

<213> ORGANISM: Artificial Sequence
<220> FEATURE:
<223> OTHER INFORMATION: Synthetic

<400> SEQUENCE: 16

Glu Val Leu Phe Arg Cys Pro Pro Cys Thr Pro Glu Arg Leu Ala Ala
1               5                   10                  15

Cys Gly Pro Pro Val Ala Pro Ala Ala Val Ala Ala Val Ala
            20                  25                  30

Gly Gly Ala Arg Met Pro Cys Ala Glu Leu Val Arg Glu Pro Gly Cys
        35                  40                  45

Gly Cys Cys Ser Val Cys Ala Arg Leu Glu Gly Glu Ala Cys Gly Val
    50                  55                  60

Tyr Thr Pro Arg Cys Gly Gln Gly Leu Arg Cys Tyr Pro His Pro Gly
65                  70                  75                  80

Ser Glu Leu Pro Leu Gln Ala Leu Val Met Gly Glu Gly Thr Cys Glu
                85                  90                  95

Lys Arg Arg Asp Ala Glu Tyr Gly Ala Ser Pro Glu Gln Val Ala Asp
            100                 105                 110

Asn Gly Asp Asp His Ser Glu Gly Gly Leu Val Glu Asn His Val Asp
        115                 120                 125

Ser Thr Met Asn Met Leu Gly Gly Gly Ser Ala Gly Arg Lys Pro
    130                 135                 140

Leu Lys Ser Gly Met Lys Glu Leu Ala Val Phe Arg Glu Lys Val Thr
145                 150                 155                 160

Glu Gln His Arg Gln Met Gly Lys Gly Gly Lys His His Leu Gly Leu
                165                 170                 175

Glu Glu Pro Lys Lys Leu Arg Pro Pro Ala Arg Thr Pro Cys Gln
            180                 185                 190

Gln Glu Leu Asp Gln Val Leu Glu Arg Ile Ser Thr Met Arg Leu Pro
        195                 200                 205

Asp Glu Arg Gly Pro Leu Glu His Leu Tyr Ser Leu His Ile Pro Asn
    210                 215                 220

Cys Asp Lys His Gly Leu Tyr Asn Leu Lys Gln Cys Lys Met Ser Leu
225                 230                 235                 240

Asn Gly Gln Arg Gly Glu Cys Trp Cys Val Asn Pro Asn Thr Gly Lys
                245                 250                 255

Leu Ile Gln Gly Ala Pro Thr Ile Arg Gly Asp Pro Glu Cys His Leu
            260                 265                 270

Phe Tyr Asn Glu Gln Gln Glu Ala Arg Gly Val His Thr Gln Arg Met
        275                 280                 285

Gln

<210> SEQ ID NO 17
<211> LENGTH: 424
<212> TYPE: PRT
<213> ORGANISM: Artificial Sequence
<220> FEATURE:
<223> OTHER INFORMATION: Synthetic

<400> SEQUENCE: 17

His Pro Asp Arg Ile Ile Phe Pro Asn His Ala Cys Glu Asp Pro Pro
1               5                   10                  15

Ala Val Leu Leu Glu Val Gln Gly Thr Leu Gln Arg Pro Leu Val Arg
            20                  25                  30

Asp Ser Arg Thr Ser Pro Ala Asn Cys Thr Trp Leu Ile Leu Gly Ser

```
                35                  40                  45
Lys Glu Gln Thr Val Thr Ile Arg Phe Gln Lys Leu His Leu Ala Cys
 50                  55                  60

Gly Ser Glu Arg Leu Thr Leu Arg Ser Pro Leu Gln Pro Leu Ile Ser
 65                  70                  75                  80

Leu Cys Glu Ala Pro Pro Ser Pro Leu Gln Leu Pro Gly Gly Asn Val
                 85                  90                  95

Thr Ile Thr Tyr Ser Tyr Ala Gly Ala Arg Ala Pro Met Gly Gln Gly
            100                 105                 110

Phe Leu Leu Ser Tyr Ser Gln Asp Trp Leu Met Cys Leu Gln Glu Glu
        115                 120                 125

Phe Gln Cys Leu Asn His Arg Cys Val Ser Ala Val Gln Arg Cys Asp
    130                 135                 140

Gly Val Asp Ala Cys Gly Asp Gly Ser Asp Glu Ala Gly Cys Ser Ser
145                 150                 155                 160

Asp Pro Phe Pro Gly Leu Thr Pro Arg Pro Val Pro Ser Leu Pro Cys
                165                 170                 175

Asn Val Thr Leu Glu Asp Phe Tyr Gly Val Phe Ser Ser Pro Gly Tyr
            180                 185                 190

Thr His Leu Ala Ser Val Ser His Pro Gln Ser Cys His Trp Leu Leu
        195                 200                 205

Asp Pro His Asp Gly Arg Arg Leu Ala Val Arg Phe Thr Ala Leu Asp
    210                 215                 220

Leu Gly Phe Gly Asp Ala Val His Val Tyr Asp Gly Pro Gly Pro Pro
225                 230                 235                 240

Glu Ser Ser Arg Leu Leu Arg Ser Leu Thr His Phe Ser Asn Gly Lys
                245                 250                 255

Ala Val Thr Val Glu Thr Leu Ser Gly Gln Ala Val Val Ser Tyr His
            260                 265                 270

Thr Val Ala Trp Ser Asn Gly Arg Gly Phe Asn Ala Thr Tyr His Val
        275                 280                 285

Arg Gly Tyr Cys Leu Pro Trp Asp Arg Pro Cys Gly Leu Gly Ser Gly
    290                 295                 300

Leu Gly Ala Gly Glu Gly Leu Gly Glu Arg Cys Tyr Ser Glu Ala Gln
305                 310                 315                 320

Arg Cys Asp Gly Ser Trp Asp Cys Ala Asp Gly Thr Asp Glu Glu Asp
                325                 330                 335

Cys Pro Gly Cys Pro Pro Gly His Phe Pro Cys Gly Ala Ala Gly Thr
            340                 345                 350

Ser Gly Ala Thr Ala Cys Tyr Leu Pro Ala Asp Arg Cys Asn Tyr Gln
        355                 360                 365

Thr Phe Cys Ala Asp Gly Ala Asp Glu Arg Arg Cys Arg His Cys Gln
    370                 375                 380

Pro Gly Asn Phe Arg Cys Arg Asp Glu Lys Cys Val Tyr Glu Thr Trp
385                 390                 395                 400

Val Cys Asp Gly Gln Pro Asp Cys Ala Asp Gly Ser Asp Glu Trp Asp
                405                 410                 415

Cys Ser Tyr Val Leu Pro Arg Lys
            420

<210> SEQ ID NO 18
<211> LENGTH: 171
<212> TYPE: PRT
<213> ORGANISM: Artificial Sequence
```

<220> FEATURE:
<223> OTHER INFORMATION: Synthetic

<400> SEQUENCE: 18

Ala Asp Arg Glu Arg Ser Ile His Asp Phe Cys Leu Val Ser Lys Val
1               5                   10                  15

Val Gly Arg Cys Arg Ala Ser Met Pro Arg Trp Trp Tyr Asn Val Thr
            20                  25                  30

Asp Gly Ser Cys Gln Leu Phe Val Tyr Gly Cys Asp Gly Asn Ser
        35                  40                  45

Asn Asn Tyr Leu Thr Lys Glu Glu Cys Leu Lys Lys Cys Ala Thr Val
50                  55                  60

Thr Glu Asn Ala Thr Gly Asp Leu Ala Thr Ser Arg Asn Ala Ala Asp
65                  70                  75                  80

Ser Ser Val Pro Ser Ala Pro Arg Arg Gln Asp Ser Glu Asp His Ser
                85                  90                  95

Ser Asp Met Phe Asn Tyr Glu Glu Tyr Cys Thr Ala Asn Ala Val Thr
            100                 105                 110

Gly Pro Cys Arg Ala Ser Phe Pro Arg Trp Tyr Phe Asp Val Glu Arg
        115                 120                 125

Asn Ser Cys Asn Asn Phe Ile Tyr Gly Gly Cys Arg Gly Asn Lys Asn
130                 135                 140

Ser Tyr Arg Ser Glu Glu Ala Cys Met Leu Arg Cys Phe Arg Gln Gln
145                 150                 155                 160

Glu Asn Pro Pro Leu Pro Leu Gly Ser Lys Val
                165                 170

<210> SEQ ID NO 19
<211> LENGTH: 758
<212> TYPE: PRT
<213> ORGANISM: Artificial Sequence
<220> FEATURE:
<223> OTHER INFORMATION: Synthetic

<400> SEQUENCE: 19

Gln Glu Ser Cys Ser Met Arg Cys Gly Ala Leu Asp Gly Pro Cys Ser
1               5                   10                  15

Cys His Pro Thr Cys Ser Gly Leu Gly Thr Cys Cys Leu Asp Phe Arg
            20                  25                  30

Asp Phe Cys Leu Glu Ile Leu Pro Tyr Ser Gly Ser Met Met Gly Gly
        35                  40                  45

Lys Asp Phe Val Val Arg His Phe Lys Met Ser Ser Pro Thr Asp Ala
50                  55                  60

Ser Val Ile Cys Arg Phe Lys Asp Ser Ile Gln Thr Leu Gly His Val
65                  70                  75                  80

Asp Ser Ser Gly Gln Val His Cys Val Ser Pro Leu Leu Tyr Glu Ser
                85                  90                  95

Gly Arg Ile Pro Phe Thr Val Ser Leu Asp Asn Gly His Ser Phe Pro
            100                 105                 110

Arg Ala Gly Thr Trp Leu Ala Val His Pro Asn Lys Val Ser Met Met
        115                 120                 125

Glu Lys Ser Glu Leu Val Asn Glu Thr Arg Trp Gln Tyr Tyr Gly Thr
130                 135                 140

Ala Asn Thr Ser Gly Asn Leu Ser Leu Thr Trp His Val Lys Ser Leu
145                 150                 155                 160

Pro Thr Gln Thr Ile Thr Ile Glu Leu Trp Gly Tyr Glu Glu Thr Gly

-continued

```
                165                 170                 175
Met Pro Tyr Ser Gln Glu Trp Thr Ala Lys Trp Ser Tyr Leu Tyr Pro
                180                 185                 190

Leu Ala Thr His Ile Pro Asn Ser Gly Ser Phe Thr Phe Thr Pro Lys
                195                 200                 205

Pro Ala Pro Pro Ser Tyr Gln Arg Trp Arg Val Gly Ala Leu Arg Ile
            210                 215                 220

Ile Asp Ser Lys Asn Tyr Ala Gly Gln Lys Asp Val Gln Ala Leu Trp
225                 230                 235                 240

Thr Asn Asp His Ala Leu Ala Trp His Leu Ser Asp Asp Phe Arg Glu
                245                 250                 255

Asp Pro Val Ala Trp Ala Arg Thr Gln Cys Gln Ala Trp Glu Glu Leu
                260                 265                 270

Glu Asp Gln Leu Pro Asn Phe Leu Glu Glu Leu Pro Asp Cys Pro Cys
            275                 280                 285

Thr Leu Thr Gln Ala Arg Ala Asp Ser Gly Arg Phe Phe Thr Asp Tyr
            290                 295                 300

Gly Cys Asp Met Glu Gln Gly Ser Val Cys Thr Tyr His Pro Gly Ala
305                 310                 315                 320

Val His Cys Val Arg Ser Val Gln Ala Ser Leu Arg Tyr Gly Ser Gly
                325                 330                 335

Gln Gln Cys Cys Tyr Thr Ala Asp Gly Thr Gln Leu Leu Thr Ala Asp
            340                 345                 350

Ser Ser Gly Gly Ser Thr Pro Asp Arg Gly His Asp Trp Gly Ala Pro
            355                 360                 365

Pro Phe Arg Thr Pro Arg Val Pro Ser Met Ser His Trp Leu Tyr
            370                 375                 380

Asp Val Leu Ser Phe Tyr Tyr Cys Cys Leu Trp Ala Pro Asp Cys Pro
385                 390                 395                 400

Arg Tyr Met Gln Arg Arg Pro Ser Asn Asp Cys Arg Asn Tyr Arg Pro
                405                 410                 415

Pro Arg Leu Ala Ser Ala Phe Gly Asp Pro His Phe Val Thr Phe Asp
            420                 425                 430

Gly Thr Asn Phe Thr Phe Asn Gly Arg Gly Glu Tyr Val Leu Leu Glu
            435                 440                 445

Ala Ala Leu Thr Asp Leu Arg Val Gln Ala Arg Ala Gln Pro Gly Thr
            450                 455                 460

Met Ser Asn Gly Thr Glu Thr Arg Gly Thr Gly Leu Thr Ala Val Ala
465                 470                 475                 480

Val Gln Glu Gly Asn Ser Asp Val Val Glu Val Arg Leu Ala Asn Arg
                485                 490                 495

Thr Gly Gly Leu Glu Val Leu Leu Asn Gln Glu Val Leu Ser Phe Thr
            500                 505                 510

Glu Gln Ser Trp Met Asp Leu Lys Gly Met Phe Leu Ser Val Ala Ala
            515                 520                 525

Gly Asp Arg Val Ser Ile Met Leu Ala Ser Gly Ala Gly Leu Glu Val
            530                 535                 540

Ser Val Gln Gly Pro Phe Leu Ser Val Ser Val Leu Pro Glu Lys
545                 550                 555                 560

Phe Leu Thr His Thr His Gly Leu Leu Gly Thr Leu Asn Asn Asp Pro
                565                 570                 575

Thr Asp Asp Phe Thr Leu His Ser Gly Arg Val Leu Pro Pro Gly Thr
            580                 585                 590
```

-continued

Ser Pro Gln Glu Leu Phe Leu Phe Gly Ala Asn Trp Thr Val His Asn
            595                 600                 605

Ala Ser Ser Leu Leu Thr Tyr Asp Ser Trp Phe Leu Val His Asn Phe
610                 615                 620

Leu Tyr Gln Pro Lys His Asp Pro Thr Phe Glu Pro Leu Phe Pro Ser
625                 630                 635                 640

Glu Thr Thr Leu Asn Pro Ser Leu Ala Gln Glu Ala Ala Lys Leu Cys
                645                 650                 655

Gly Asp Asp His Phe Cys Asn Phe Asp Val Ala Ala Thr Gly Ser Leu
            660                 665                 670

Ser Thr Gly Thr Ala Thr Arg Val Ala His Gln Leu His Gln Arg Arg
        675                 680                 685

Met Gln Ser Leu Gln Pro Val Val Ser Cys Gly Trp Leu Ala Pro Pro
    690                 695                 700

Pro Asn Gly Gln Lys Glu Gly Asn Arg Tyr Leu Ala Gly Ser Thr Ile
705                 710                 715                 720

Tyr Phe His Cys Asp Asn Gly Tyr Ser Leu Ala Gly Ala Glu Thr Ser
                725                 730                 735

Thr Cys Gln Ala Asp Gly Thr Trp Ser Ser Pro Thr Pro Lys Cys Gln
            740                 745                 750

Pro Gly Arg Ser Tyr Ala
        755

<210> SEQ ID NO 20
<211> LENGTH: 121
<212> TYPE: PRT
<213> ORGANISM: Artificial Sequence
<220> FEATURE:
<223> OTHER INFORMATION: Synthetic

<400> SEQUENCE: 20

Trp Ser Pro Gln Glu Glu Asp Arg Ile Ile Glu Gly Gly Ile Tyr Asp
1               5                   10                  15

Ala Asp Leu Asn Asp Glu Arg Val Gln Arg Ala Leu His Phe Val Ile
            20                  25                  30

Ser Glu Tyr Asn Lys Ala Thr Glu Asp Glu Tyr Tyr Arg Arg Leu Leu
        35                  40                  45

Arg Val Leu Arg Ala Arg Glu Gln Ile Val Gly Gly Val Asn Tyr Phe
    50                  55                  60

Phe Asp Ile Glu Val Gly Arg Thr Ile Cys Thr Lys Ser Gln Pro Asn
65                  70                  75                  80

Leu Asp Thr Cys Ala Phe His Glu Gln Pro Glu Leu Gln Lys Lys Gln
                85                  90                  95

Leu Cys Ser Phe Gln Ile Tyr Glu Val Pro Trp Glu Asp Arg Met Ser
            100                 105                 110

Leu Val Asn Ser Arg Cys Gln Glu Ala
        115                 120

<210> SEQ ID NO 21
<211> LENGTH: 29
<212> TYPE: DNA
<213> ORGANISM: Artificial Sequence
<220> FEATURE:
<223> OTHER INFORMATION: Synthetic

<400> SEQUENCE: 21
ccggatatca gcaagcccac gtgcccacc                                         29

```
<210> SEQ ID NO 22
<211> LENGTH: 40
<212> TYPE: DNA
<213> ORGANISM: Artificial Sequence
<220> FEATURE:
<223> OTHER INFORMATION: Synthetic

<400> SEQUENCE: 22
aaggaaaaaa gcggccgctc atttacccgg agagcgggag                           40

<210> SEQ ID NO 23
<211> LENGTH: 34
<212> TYPE: DNA
<213> ORGANISM: Artificial Sequence
<220> FEATURE:
<223> OTHER INFORMATION: Synthetic

<400> SEQUENCE: 23
cccaagcttg cagcacccaa gtgtgcaccg gcac                                 34

<210> SEQ ID NO 24
<211> LENGTH: 37
<212> TYPE: DNA
<213> ORGANISM: Artificial Sequence
<220> FEATURE:
<223> OTHER INFORMATION: Synthetic

<400> SEQUENCE: 24
gtgctcgagt cacgtcagag ggctggctct ctgctcg                              37
```

REAGENTS AND METHODS FOR BREAST CANCER DETECTION

CROSS REFERENCE

This application claims priority to U.S. Provisional Patent Application Ser. No. 61/954,914 filed Mar. 18, 2014, incorporated by reference herein in its entirety.

STATEMENT REGARDING FEDERALLY SPONSORED RESEARCH OR DEVELOPMENT

This invention was made with government support under Grant No. P20GM103548awarded by the National Institutes of Health (NIH). The government has certain rights in the invention.

BACKGROUND

For patients with breast cancer (BCa), early and personalized diagnosis is crucial for optimizing treatments leading to long-term survival. Although mammography is the most widely used method to detect BCa, approximately 20% of screening mammograms result in a false negative diagnosis largely due to high breast density. Additionally, 1 in 10 women who get a mammogram will need additional imaging. Yet, the overwhelming majority of these women will not have BCa, as only 2 to 4 of every 1,000 screening mammograms leads to a cancer diagnosis. Therefore, there is an urgent clinical need to develop a novel, minimally invasive diagnostic strategy for the early diagnosis and monitoring of BCa.

SUMMARY OF THE INVENTION

In a first aspect, the invention provides compositions consisting of between 2 and 25 antibody detection markers, wherein the composition includes reagents for detecting human autoantibodies against at least two proteins selected from the group consisting of human ANGPTL4, DKK1, EPHA2, LAMC2, SPON2, SSR2, GAL1, GFRA1, LRRC15, CD147, CD320, CDH3, LRP10, SPINT2, SUSD2, and CST2. In one embodiment, the composition includes reagents for detecting human autoantibodies against at least two proteins selected from the group consisting of human ANGPTL4, DKK1, EPHA2, GAL1, LAMC2, SPON2, CST2, SPINT2 and SSR2. In a further embodiment, the composition includes reagents for detecting human autoantibodies against at least 5 proteins in the recited group. In another embodiment, the composition further includes reagents for detecting human autoantibodies against one or both of MUC1 and GRN. In various embodiments, the composition consists of between 2 and 20, 4 and 10, and 5-10 antibody detection markers. In various further embodiments, the composition includes reagents for detecting human autoantibodies against one of the following marker sets:
ANGPTL4, DKK1, GAL1, GFRA1, GRANULIN, LRRC15, and MUC1;
ANGPTL4, DKK1, GAL1, GRANULIN, LRRC15, and MUC1;
ANGPTL4, DKK1, GAL1, and LRRC15;
ANGPTL4, DKK1, GAL1, GFRA1, and LRRC15;
DKK1, GAL1, GFRA1, GRANULIN, LRRC1, and 5 MUC1;
ANGPTL4, DKK1, GAL1, GFRA1, GRANULIN, and LRRC15;
DKK1, GAL1, GRANULIN, LRRC15, and MUC1;
DKK1, GAL1, GFRA1, GRANULIN, and LRRC15;
DKK1, GAL1, GFRA1, LRRC15, and MUC1;
ANGPTL4, DKK1, GAL1, GRANULIN, and LRRC15;
DKK1, GAL1, GFRA1, and LRRC15;
DKK1, GAL1, GRANULIN, and LRRC15;
ANGPTL4, DKK1, GAL1, LRRC15, and MUC1;
DKK1, GAL1, and LRRC15;
ANGPTL4, GAL1, LRRC15, and MUC1;
GAL1, GFRA1, LRRC15, and MUC1;
GAL1, GFRA1, and LRRC15;
ANGPTL4, GAL1, and LRRC15;
DKK1, GAL1, LRRC15, and MUC1;
ANGPTL4, GAL1, GFRA1, and LRRC15;
GAL1, LRRC15, and MUC1;
ANGPTL4, GAL1, GFRA1, LRRC15, and MUC1;
ANGPTL4, GAL1, and GFRA1;
DKK1, GAL1, and GFRA1; and
GAL1, GFRA1, and MUC1.

In another embodiment, the reagents for detecting human autoantibodies comprise the at least two proteins, or antigenic fragments thereof. In a further embodiment, the at least two proteins, or antigenic fragments thereof comprise native extracellular domains and/or native secreted proteins or antigenic fragments thereof. In a still further embodiment, the reagents are detectably labeled. In another embodiment, reagents are immobilized on a surface.

In another aspect, the invention provides methods for detecting breast cancer or disease recurrence, comprising contacting a bodily fluid sample from a subject at risk of having breast cancer or breast cancer recurrence with one or more reagents for detecting autoantibodies against one or more of human ANGPTL4, DKK1, EPHA2, LAMC2, SPON2, SSR2, GAL1, GFRA1, LRRC15, CD147, CD320, CDH3, LRP10, SPINT2, SUSD2, and CST2, wherein the presence of autoantibodies against the one or more proteins correlates with a likelihood of the subject having breast cancer or breast cancer recurrence. In another embodiment, the reagents comprise reagents for detecting autoantibodies against one or more of human ANGPTL4, DKK1, EPHA2, GAL1, LAMC2, SPON2, CST2, SPINT2 and SSR2. In various further embodiments, the reagents comprise reagents for detecting autoantibodies two or more, or five or more of the recited proteins. In another embodiment the reagents comprise reagents for detecting human autoantibodies against one of the following marker sets:
ANGPTL4, DKK1, GAL1, GFRA1, GRANULIN, LRRC15, and MUC1;
ANGPTL4, DKK1, GAL1, GRANULIN, LRRC15, and MUC1;
ANGPTL4, DKK1, GAL1, and LRRC15;
ANGPTL4, DKK1, GAL1, GFRA1, and LRRC15;
DKK1, GAL1, GFRA1, GRANULIN, LRRC1, and 5 MUC1;
ANGPTL4, DKK1, GAL1, GFRA1, GRANULIN, and LRRC15;
DKK1, GAL1, GRANULIN, LRRC15, and MUC1;
DKK1, GAL1, GFRA1, GRANULIN, and LRRC15;
DKK1, GAL1, GFRA1, LRRC15, and MUC1;
ANGPTL4, DKK1, GAL1, GRANULIN, and LRRC15;
DKK1, GAL1, GFRA1, and LRRC15;
DKK1, GAL1, GRANULIN, and LRRC15;
ANGPTL4, DKK1, GAL1, LRRC15, and MUC1;
DKK1, GAL1, and LRRC15;
ANGPTL4, GAL1, LRRC15, and MUC1;
GAL1, GFRA1, LRRC15, and MUC1;
GAL1, GFRA1, and LRRC15;

ANGPTL4, GAL1, and LRRC15;
DKK1, GAL1, LRRC15, and MUC1;
ANGPTL4, GAL1, GFRA1, and LRRC15;
GAL1, LRRC15, and MUC1;
ANGPTL4, GAL1, GFRA1, LRRC15, and MUC1;
ANGPTL4, GAL1, and GFRA1;
DKK1, GAL1, and GFRA1; and
GAL1, GFRA1, and MUC1.

In a further embodiment, the reagents comprise reagents for detecting human autoantibodies against human ANGPTL4, DKK1, GAL1, MUC1, GFRA1, GRN and LRRC15. In another embodiment, the one or more reagents comprise the composition of any embodiment or combination of embodiments of the invention. In a further embodiment, the contacting comprises use of ELISA. In another embodiment, the bodily fluid sample comprises a serum sample from the subject. In a further embodiment, the method identifies the subject as likely to have breast cancer or breast cancer recurrence. In a further embodiment, the method further comprises treating the subject with an amount of a therapeutic sufficient to treat the breast cancer or breast cancer recurrence.

In a further aspect, the invention provides methods for treating a subject with breast cancer, comprising:
(a) testing a bodily fluid sample from a subject at risk of breast cancer, and identifying candidate subjects that:
  (i) have autoantibodies against at least one of ANGPTL4, DKK1, GAL1, MUC1, GFRA1, GRN and LRRC15; and/or
  (ii) do not have autoantibodies against GFRA1, GRN and/or LRRC15; and
(b) treating the candidate subjects with an amount of a therapeutic sufficient to treat the breast cancer.

In one embodiment, the contacting comprises use of Longitudinal Assay Screening, wherein all target biomarkers may be detected and quantitated within a single test and dilution. In a further embodiment, the bodily fluid sample comprises a blood sample from the subject.

DETAILED DESCRIPTION OF THE INVENTION

Figure 1:
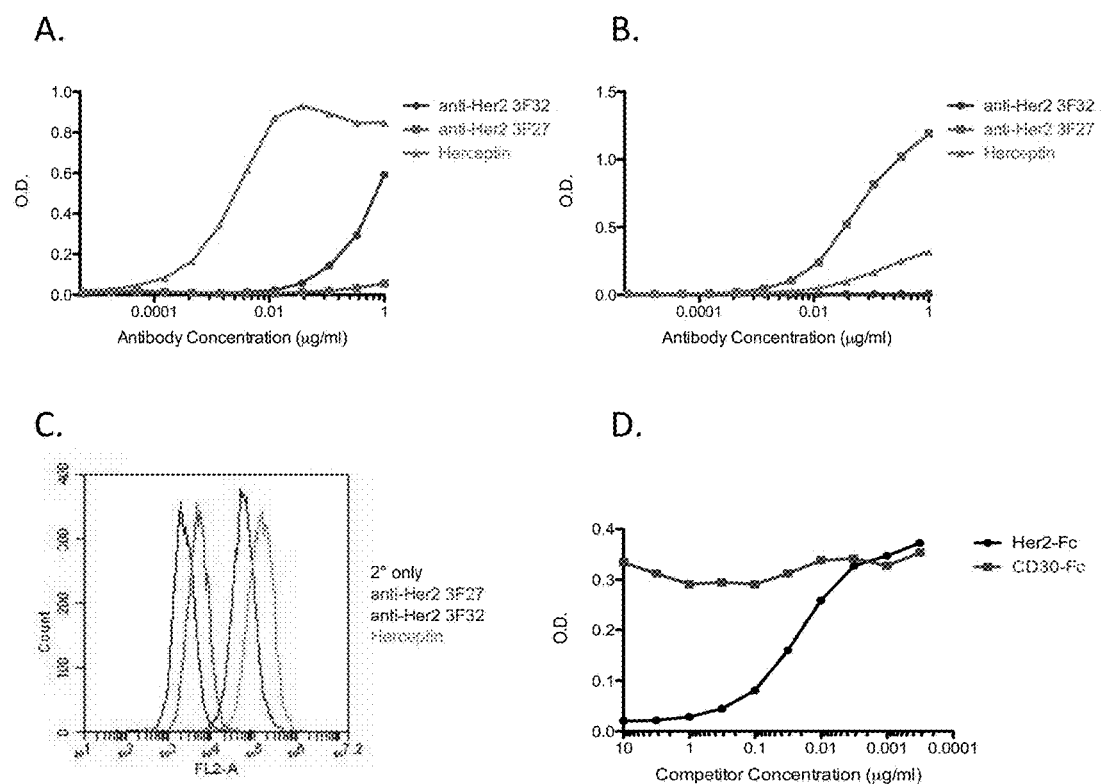
FIG. 1. Antigen conformation affects antibody recognition. A, ELISA analysis using an antigen designed to have native conformation. Wells were coated with anti-rabbit IgG followed by the HER-2-ECD-rFc protein generated in 293T cells. Serial dilutions of anti-HER-2 monoclonal antibodies generated against native HER-2, 3F32 (blue), Herceptin (green) or against denatured HER-2, 3F27 (red) were used in ELISA. Reactions were developed after addition of the appropriate secondary antibody. The O.D. is the absorbance reading for the reaction. B, ELISA analysis using a denatured antigen. Wells were coated with purified His-HER-2-ECD generated in *E. coli*, and serial dilutions of 3F32 (blue), Herceptin (green) or 3F27 (red) were added. After addition of the secondary antibody, the reactions were developed. C, detection of native HER-2 on SKBR3 cells via flow cytometry. Fluorescence indicates antibody recognition of HER-2 on the surface of SKBR3 cells. D, binding competition assay to demonstrate specificity of conformation-carrying antigen ELISA. Wells were precoated with anti-rabbit IgG followed by HER-2-ECD-rFc. Purified HER-2-Fc (black) or CD30-Fc (purple) chimeric proteins were serially diluted and added to a constant amount of Herceptin before addition to the wells. The reactions were developed after incubation with the secondary antibody.

All references cited are herein incorporated by reference in their entirety.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, 2nd Ed.* (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

In a first aspect, the present invention provides compositions consisting of between 2 and 25 antibody detection markers, wherein the composition includes reagents for detecting human autoantibodies against at least two proteins selected from the group consisting of human ANGPTL4, DKK1, EPHA2, LAMC2, SPON2, SSR2, GAL1, GFRA1, LRRC15, CD147, CD320, CDH3, LRP10, SPINT2, SUSD2, and CST2. The inventors have unexpectedly discovered that autoantibodies against the recited proteins provide an indication of whether a subject is suffering from breast cancer (BCa). Thus, the compositions of the invention can be used, for example, in diagnostic assays to discriminate between BCa and healthy patients by the detection of antibodies in a sample from the subject or to detect recurrence of disease in a breast cancer patient after treatment. In one embodiment, the composition includes reagents for detecting human autoantibodies against at least two proteins selected from the group consisting of ANGPTL4, DKK1, EPHA2, GAL1, LAMC2, SPON2, CST2, SPINT2 and SSR2.

In various embodiments, the composition includes reagents for detecting human autoantibodies against at least three, four, five, six, seven, eight, nine, ten, eleven, twelve, thirteen, fourteen, fifteen, or sixteen proteins in the recited group. In various further embodiments, the composition consists of between 2-24, 2-23, 2-22, 2-21, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-25, 3-24, 3-23, 3-22, 3-21, 3-20, 3-19, 3-18, 3-17, 3-16, 3-15, 3-14, 3-13, 3-12, 3-11, 3-10, 3-9, 3-8, 3-7, 3-6, 3-5, 3-4, 4-25, 4-24, 4-23, 4-22, 4-21, 4-20, 4-19, 4-18, 4-17, 4-16, 4-15, 4-14, 4-13, 4-14, 4-13, 4-12, 4-11, 4-10, 4-9, 4-8, 4-7, 4-6, 4-5, 5-25, 5-24, 5-23, 5-22, 5-21, 5-20, 5-19, 5-18, 5-17, 5-16, 5-15, 5-14, 5-13, 5-12, 5-11, 5-10, 5-9, 5-8, 5-7, 5-6, 6-25, 6-24, 6-23, 6-22, 6-21, 6-20, 6-19, 6-18, 6-17, 6-16, 6-15, 6-14, 6-13, 6-12, 6-11, 6-10, 6-9, 6-8, 6-7, 7-25, 7-24, 7-23, 7-22, 7-21, 7-20, 7-19, 7-18, 7-17, 7-16, 7-15, 7-14, 7-13, 7-12, 7-11, 7-10, 7-9, 7-8, 8-25, 8-24, 8-23, 8-22, 8-21, 8-20, 8-19, 8-18, 8-17, 8-16, 8-15, 8-14, 8-13, 8-12, 8-11, 8-10, 8-9, 9-25, 9-24, 9-23, 9-22, 9-21, 9-20, 9-19, 9-18, 9-17, 9-16, 9-15, 9-14, 9-13, 9-12, 9-11, 9-10, 1, 2, 3, 4, 5, 6, 7, 8, 9, 10-11, 12, 13, 14, 15, or 16 antibody detection reagents.

As will be understood by those of skill in the art, the compositions may include additional antibody detection markers and controls as is appropriate for an intended use of the composition. In one non-limiting embodiment, the compositions may further comprise reagents for detecting antibodies against one or both of mucin-1(MUC1), HER-2 (41), IGFBP2, and GRANULIN (GRN).

In further embodiments, the compositions comprise or consist of reagents for detecting human autoantibodies against one of the following marker sets, which are shown in the examples that follow (see Table 5) to provide strong predictive value for diagnosing breast cancer:
ANGPTL4, DKK1, GAL1, GFRA1, GRANULIN, LRRC15, and MUC1;
ANGPTL4, DKK1, GAL1, GRANULIN, LRRC15, and MUC1;
ANGPTL4, DKK1, GAL1, and LRRC15;
ANGPTL4, DKK1, GAL1, GFRA1, and LRRC15;
DKK1, GAL1, GFRA1, GRANULIN, LRRC1, and MUC1;
ANGPTL4, DKK1, GAL1, GFRA1, GRANULIN, and LRRC15;
DKK1, GAL1, GRANULIN, LRRC15, and MUC1;
DKK1, GAL1, GFRA1, GRANULIN, and LRRC15;
DKK1, GAL1, GFRA1, LRRC15, and MUC1;
ANGPTL4, DKK1, GAL1, GRANULIN, and LRRC15;
DKK1, GAL1, GFRA1, and LRRC15;
DKK1, GAL1, GRANULIN, and LRRC15;
ANGPTL4, DKK1, GAL1, LRRC15, and MUC1;
DKK1, GAL1, and LRRC15;
ANGPTL4, GAL1, LRRC15, and MUC1;
GAL1, GFRA1, LRRC15, and MUC1;
GAL1, GFRA1, and LRRC15;
ANGPTL4, GAL1, and LRRC15;
DKK1, GAL1, LRRC15, and MUC1;
ANGPTL4, GAL1, GFRA1, and LRRC15;
GAL1, LRRC15, and MUC1;
ANGPTL4, GAL1, GFRA1, LRRC15, and MUC1;
ANGPTL4, GAL1, and GFRA1;
DKK1, GAL1, and GFRA1; and
GAL1, GFRA1, and MUC1.

In another embodiment, the compositions comprise or consist of reagents for detecting human autoantibodies against human ANGPTL4, DKK1, GAL1, MUC1, GFRA1, GRN and LRRC15.

The antibody detection markers may be any suitable reagents that can be used to detect antibodies against the recited proteins, including but not limited to the recited protein, a secreted version of the protein (such as a native secreted form of the protein), or an extracellular domain of the protein. Secreted proteins are more easily delivered from tumor cells to lymph nodes, where interactions of immune cells take place resulting in abundant high-affinity antibodies. Membrane surface proteins are commonly released in a soluble form from tumor cells through metalloproteinase-dependent cleavage. The shed proteins are more easily transferred to the lymph nodes than intracellular protein. Thus, in one embodiment the antibody detection marker is a secreted or membrane portion of the recited protein. Exemplary amino acid sequences of the secreted or membrane portion of the recited human proteins are shown below.

ANGPTL4
(SEQ ID NO: 1)
KSPRFASWDEMNVLAHGLLQLGQGLREHAERTRSQLSALERRLSACG

SACQGTEGSTDLPLAPESRVDPEVLHSLQTQLKAQNSRIQQLFHKVA

QQQRHLEKQHLRIQHLQSQFGLLDHKHLDHEVAKPARRKRLPEMAQP

VDPAHNVSRLHRLPRDCQELFQVGERQSGLFEIQPQGSPPFLVNCKM

TSDGGWTVIQRRHDGSVDFNRPWEAYKAGFGDPHGEFWLGLEKVHSI

TGDRNSRLAVQLRDWDGNAELLQFSVHLGGEDTAYSLQLTAPVAGQL

GATTVPPSGLSVPFSTWDQDHDLRRDKNCAKSLSGGWWFGTCSHSNL

NGQYFRSIPQQRQKLKKGIFWKTWRGRYYPLQATTMLIQPMAAEAAS

DKK1
(SEQ ID NO: 2)
VSATLNSVLNSNAIKNLPPPLGGAAGHPGSAVSAAPGILYPGGNKYQ

TIDNYQPYPCAEDEECGTDEYCASPTRGGDAGVQICLACRKRRKRCM

RHAMCCPGNYCKNGICVSSDQNHFRGEIEETITESFGNDHSTLDGYS

RRTTLSSKMYHTKGQEGSVCLRSSDCASGLCCARHFWSKICKPVLKE

GQVCTKHRRKGSHGLEIFQRCYCGEGLSCRIQKDHHQASNSSRLHTC

QRH

EPHA2
(SEQ ID NO: 3)
KEVVLLDFAAAGGELGWLTHPYGKGWDLMQNIMNDMPIYMYSVCNVM

SGDQDNWLRTNWVYRGEAERIFIELKFTVRDCNSFPGGASSCKETFN

LYYAESDLDYGTNFQKRLFTKIDTIAPDEITVSSDFEARHVKLNVEE

RSVGPLTRKGFYLAFQDIGACVALLSVRVYYKKCPELLQGLAHFPET

IAGSDAPSLATVAGTCVDHAVVPPGGEEPRMHCAVDGEWLVPIGQCL

CQAGYEKVEDACQACSPGFFKFEASESPCLECPEHTLPSPEGATSCE

CEEGFFRAPQDPASMPCTRPPSAPHYLTAVGMGAKVELRWTPPQDSG

GREDIVYSVTCEQCWPESGECGPCEASVRYSEPPHGLTRTSVTVSDL

EPHMNYTFTVEARNGVSGLVTSRSFRTASVSINQTEPPKVRLEGRST

TSLSVSWSIPPPQQSRVWKYEVTYRKKGDSNSYNVRRTEGFSVTLDD

LAPDTTYLVQVQALTQEGQGAGSKVHEFQTLSPEGSGNL

LAMC2
(SEQ ID NO: 4)
TSRREVCDCNGKSRQCIFDRELHRQTGNGFRCLNCNDNTDGIHCEKC

KNGFYRHRERDRCLPCNCNSKGSLSARCDNSGRCSCKPGVTGARCDR

CLPGFHMLTDAGCTQDQRLLDSKCDCDPAGIAGPCDAGRCVCKPAVT

GERCDRCRSGYYNLDGGNPEGCTQCFCYGHSASCRSSAEYSVHKITS

TFHQDVDGWKAVQRNGSPAKLQWSQRHQDVFSSAQRLDPVYFVAPAK

FLGNQQVSYGQSLSFDYRVDRGGRHPSAHDVILEGAGLRITAPLMPL

GKTLPCGLTKTYTFRLNEHPSNNWSPQLSYFEYRRLLRNLTALRIRA

TYGEYSTGYIDNVTLISARPVSGAPAPWVEQCICPVGYKGQFCQDCA

SGYKRDSARLGPFGTCIPCNCQGGGACDPDTGDCYSGDENPDIECAD

CPIGFYNDPHDPRSCKPCPCHNGFSCSVMPETEEVVCNNCPPGVTGA

RCELCADGYFGDPFGEHGPVRPCQPCQCNNNVDPSASGNCDRLTGRC

LKCIHNTAGIYCDQCKAGYFGDPLAPNPADKCRACNCNPMGSEPVGC

-continued

RSDGTCVCKPGFGGPNCEHGAFSCPACYNQVKIQMDQFMQQLQRMEA

LISKAQGGDGVVPDTELEGRMQQAEQALQDILRDAQISEGASRSLGL

QLAKVRSQENSYQSRLDDLKMTVERVRALGSQYQNRVRDTHRLITQM

QLSLAESEASLGNTNIPASDHYVGPNGFKSLAQEATRLAESHVESAS

NMEQLTRETEDYSKQALSLVRKALHEGVGSGSGSPDGAVVQGLVEKL

EKTKSLAQQLTREATQAEIEADRSYQHSLRLLDSVSRLQGVSDQSFQ

VEEAKRIKQKADSLSSLVTRHMDEFKRTQKNLGNWKEEAQQLLQNGK

SGREKSDQLLSRANLAKSRAQEALSMGNATFYEVESILKNLREFDLQ

VDNRKAEAEEAMKRLSYISQKVSDASDKTQQAERALGSAAADAQRAK

NGAGEALEISSEIEQEIGSLNLEANVTADGALAMEKGLASLKSEMRE

VEGELERKELEFDTNMDAVQMVITEAQKVDTRAKNAGVTIQDTLNTL

DGLLHLMGM

SPON2

(SEQ ID NO: 5)

QPLGGESICSARAPAKYSITFTGKWSQTAFPKQYPLFRPPAQWSSLL

GAAHSSDYSMWRKNQYVSNGLRDFAERGEAWALMKEIEAAGEALQSV

HEVFSAPAVPSGTGQTSAELEVQRRHSLVSFVVRIVPSPDWFVGVDS

LDLCDGDRWREQAALDLYPYDAGTDSGFTFSSPNFATIPQDTVTEIT

SSSPSHPANSFYYPRLKALPPIARVTLLRLRQSPRAFIPPAPVLPSR

DNEIVDSASVPETPLDCEVSLWSSWGLCGGHCGRLGTKSRTRYVRVQ

PANNGSPCPELEEEAECVPDNCV

SSR2

(SEQ ID NO: 6)

EEGARLLASKSLLNRYAVEGRDLTLQYNIYNVGSSAALDVELSDDSF

PPEDFGIVSGMLNVKWDRIAPASNVSHTVVLRPLKAGYFNFTSATIT

YLAQEDGPVVIGSTSAPGQGGILAQREFDRRFSPH

GAL1

(SEQ ID NO: 7)

LRVRGEVAPDAKSFVLNLGKDSNNLCLHFNPRFNAHGDANTIVCNSK

DGGAWGTEQREAVFPFQPGSVAEVCITFDQANLTVKLPDGYEFKFPN

RLNLEAINYMAADGDFKIKCVAFD

GFRA1

(SEQ ID NO: 8)

DRLDCVKASDQCLKEQSCSTKYRTLRQCVAGKETNFSLASGLEAKDE

CRSAMEALKQKSLYNCRCKRGMKKEKNCLRIYWSMYQSLQGNDLLED

SPYEPVNSRLSDIFRVVPFISDVFQQVEHIPKGNNCLDAAKACNLDD

ICKKYRSAYITPCTTSVSNDVCNRRKCHKALRQFFDKVPAKHSYGML

FCSCRDIACTERRRQTIVPVCSYEEREKPNCLNLQDSCKTNYICRSR

LADFFTNCQPESRSVSSCLKENYADCLLAYSGLIGTVMTPNYIDSSS

LSVAPWCDCSNSGNDLEECLKFLNFFKDNTCLKNAIQAFGNGSDVTV

WQPAFPVQTTTATTTTALRVKNKPLGPAGSENEIPTHVLPPCANLQA

QKLKSNVSGNTHLCISNGNYEKEGLGASSHITTKSMAAPPSCGLSPL

LVLVVTALSTLLSLTETS

LRRC15

(SEQ ID NO: 9)

YHGCPSECTCSRASQVECTGARIVAVPTPLPWNAMSLQILNTHITEL

NESPFLNISALIALRIEKNELSRITPGAFRNLGSLRYLSLANNKLQV

LPIGLFQGLDSLESLLLSSNQLLQIQPAHFSQCSNLKELQLHGNHLE

YIPDGAFDHLVGLTKLNLGKNSLTHISPRVFQHLGNLQVLRLYENRL

TDIPMGTFDGLVNLQELALQQNQIGLLSPGLFHNNHNLQRLYLSNNH

ISQLPPSVFMQLPQLNRLTLFGNSLKELSPGIFGPMPNLRELWLYDN

HISSLPDNVFSNLRQLQVLILSRNQISFISPGAFNGLTELRELSLHT

NALQDLDGNVFRMLANLQNISLQNNRLRQLPGNIFANVNGLMAIQLQ

NNQLENLPLGIFDHLGKLCELRLYDNPWRCDSDILPLRNWLLLNQPR

LGTDTVPVCFSPANVRGQSLIIINVNVAVPSVHVPEVPSYPETPWYP

DTPSYPDTTSVSSTTELTSPVEDYTDLTTIQVTDDRSVWGMTQAQSG

GRN (SEQ ID NO: 10)

TRCPDGQFCPVACCLDPGGASYSCCRPLLDKWPTTLSRHLGGPCQVD

AHCSAGHSCIFTVSGTSSCCPFPEAVACGDGHHCCPRGFHCSADGRS

CFQRSGNNSVGAIQCPDSQFECPDFSTCCVMVDGSWGCCPMPQASCC

EDRVHCCPHGAFCDLVHTRCITPTGTHPLAKKLPAQRTNRAVALSSS

VMCPDARSRCPDGSTCCELPSGKYGCCPMPNATCCSDHLHCCPQDTV

CDLIQSKCLSKENATTDLLTKLPAHTVGDVKCDMEVSCPDGYTCCRL

QSGAWGCCPFTQAVCCEDHIHCCPAGFTCDTQKGTCEQGPHQVPWME

KAPAHLSLPDPQALKRDVPCDNVSSCPSSDTCCQLTSGEWGCCPIPE

AVCCSDHQHCCPQGYTCVAEGQCQRGSEIVAGLEKMPARRASLSHPR

DIGCDQHTSCPVGQTCCPSLGGSWACCQLPHAVCCEDRQHCCPAGYT

CNVKARSCEKEVVSAQPATFLARSPHVGVKDVECGEGHFCHDNQTCC

RDNRQGWACCPYRQGVCCADRRHCCPAGFRCAARGTKCLRREAPRWD

APLRDPALRQLL

MUC1

(SEQ ID NO: 11)

APKPATVVTGSGHASSTPGGEKETSATQRSSVPSSTEKNAFNSSLED

PSTDYYQELQRDISEMFLQIYKQGGFLGLSNIKFRPGSVVVQLTLAF

REGTINVHDVETQFNQYKTEAASRYNLTISDVSVSDVPFPFSAQSGA

GVPG

CD147

(SEQ ID NO: 12)

AAGTVFTTVEDLGSKILLTCSLNDSATEVTGHRWLKGGVVLKEDALP

GQKTEFKVDSDDQWGEYSCVFLPEPMGTANIQLHGPPRVKAVKSSEH

INEGETAMLVCKSESVPPVTDWAWYKITDSEDKALMNGSESRFFVSS

CD320

(SEQ ID NO: 13)

AGPSSGSCPPTKFQCRTSGLCVPLTWRCDRDLDCSDGSDEEECRIEP

CTQKGQCPPPPGLPCPCTGVSDCSGGTDKKLRNCSRLACLAGELRCT

LSDDCIPLTWRCDGHPDCPDSSDELGCGTNEILPEGDATTMGPPVTL

ESVTSLRNATTMGPPVTLESVPSVGNATSSSAGDQSGSPTAYG

CDH3
(SEQ ID NO: 14)
EPCRAVFREAEVTLEAGGAEQEPGQALGKVFMGCPGQEPALFSTDND
DFTVRNGETVQERRSLKERNPLKIFPSKRILRRHKRDWVVAPISVPE
NGKGPFPQRLNQLKSNKDRDTKIFYSITGPGADSPPEGVFAVEKETG
WLLLNKPLDREEIAKYELFGHAVSENGASVEDPMNISIIVTDQNDHK
PKFTQDTFRGSVLEGVLPGTSVMQMTATDEDDAIYTYNGVVAYSIHS
QEPKDPHDLMFTIHRSTGTISVISSGLDREKVPEYTLTIQATDMDGD
GSTTTAVAVVEILDANDNAPMFDPQKYEAHVPENAVGHEVQRLTVTD
LDAPNSPAWRATYLIMGGDDGDHFTITTHPESNQGILTTRKGLDFEA
KNQHTLYVEVTNEAPFVLKLPTSTATIVVHVEDVNEAPVFVPPSKVV
EVQEGIPTGEPVCVYTAEDPDKENQKISYRILRDPAGWLAMDPDSGQ
VTAVGTLDREDEQFVRNNIYEVMVLAMDNGSPPTTGTGTLLLTLIDV
NDHGPVPEPRQITICNQSPVRQVLNITDKDLSPHTSPFQAQLTDDSD
IYWTAEVNEEGDTVVLSLKKFLKQDTYDVHLSLSDHGNKEQLTVIRA
TVCDCHGHVETCPGPWKGG

HER2
(SEQ ID NO: 15)
TQVCTGTDMKLRLPASPETHLDMLRHLYQGCQVVQGNLELTYLPTNA
SLSFLQDIQEVQGYVLIAHNQVRQVPLQRLRIVRGTQLFEDNYALAV
LDNGDPLNNTTPVTGASPGGLRELQLRSLTEILKGGVLIQRNPQLCY
QDTILWKDIFHKNNQLALTLIDTNRSRACHPCSPMCKGSRCWGESSE
DCQSLTRTVCAGGCARCKGPLPTDCCHEQCAAGCTGPKHSDCLACLH
FNHSGICELHCPALVTYNTDTFESMPNPEGRYTFGASCVTACPYNYL
STDVGSCTLVCPLHNQEVTAEDGTQRCEKCSKPCARVCYGLGMEHLR
EVRAVTSANIQEFAGCKKIFGSLAFLPESFDGDPASNTAPLQPEQLQ
VFETLEEITGYLYISAWPDSLPDLSVFQNLQVIRGRILHNGAYSLTL
QGLGISWLGLRSLRELGSGLALIHHNTHLCFVHTVPWDQLFRNPHQA
LLHTANRPEDECVGEGLACHQLCARGHCWGPGPTQCVNCSQFLRGQE
CVEECRVLQGLPREYVNARHCLPCHPECQPQNGSVTCFGPEADQCVA
CAHYKDPPFCVARCPSGVKPDLSYMPIWKFPDEEGACQPCPINCTHS
CVDLDDKGCPAEQRASPLT

IGFBP2
(SEQ ID NO: 6)
EVLFRCPPCTPERLAACGPPPVAPPAAVAAVAGGARMPCAELVREPG
CGCCSVCARLEGEACGVYTPRCGQGLRCYPHPGSELPLQALVMGEGT
CEKRRDAEYGASPEQVADNGDDHSEGGLVENHVDSTMNMLGGGGSAG
RKPLKSGMKELAVFREKVTEQHRQMGKGGKHHLGLEEPKKLRPPPAR
TPCQQELDQVLERISTMRLPDERGPLEHLYSLHIPNCDKHGLYNLKQ
CKMSLNGQRGECWCVNPNTGKLIQGAPTIRGDPECHLFYNEQQEARG
VHTQRMQ

LRP10
(SEQ ID NO: 17)
HPDRIIFPNHACEDPPAVLLEVQGTLQRPLVRDSRTSPANCTWLILG
SKEQTVTIRFQKLHLACGSERLTLRSPLQPLISLCEAPPSPLQLPGG
NVTITYSYAGARAPMGQGFLLSYSQDWLMCLQEEFQCLNHRCVSAVQ
RCDGVDACGDGSDEAGCSSDPFPGLTPRPVPSLPCNVTLEDFYGVFS
SPGYTHLASVSHPQSCHWLLDPHDGRRLAVRFTALDLGFGDAVHVYD
GPGPPESSRLLRSLTHFSNGKAVTVETLSGQAVVSYHTVAWSNGRGF
NATYHVRGYCLPWDRPCGLGSGLGAGEGLGERCYSEAQRCDGSWDCA
DGTDEEDCPGCPPGHFPCGAAGTSGATACYLPADRCNYQTFCADGAD
ERRCRHCQPGNFRCRDEKCVYETWVCDGQPDCADGSDEWDCSYVLPR
K

SPINT2
(SEQ ID NO: 18)
ADRERSIHDFCLVSKVVGRCRASMPRWWYNVTDGSCQLFVYGGCDGN
SNNYLTKEECLKKCATVTENATGDLATSRNAADSSVPSAPRRQDSED
HSSDMFNYEEYCTANAVTGPCRASFPRWYFDVERNSCNNFIYGGCRG
NKNSYRSEEACMLRCFRQQENPPLPLGSKV

SUSD2
(SEQ ID NO: 19)
QESCSMRCGALDGPCSCHPTCSGLGTCCLDFRDFCLEILPYSGSMMG
GKDFVVRHFKMSSPTDASVICRFKDSIQTLGHVDSSGQVHCVSPLLY
ESGRIPFTVSLDNGHSFPRAGTWLAVHPNKVSMMEKSELVNETRWQY
YGTANTSGNLSLTWHVKSLPTQTITIELWGYEETGMPYSQEWTAKWS
YLYPLATHIPNSGSFTFTPKPAPPSYQRWRVGALRIIDSKNYAGQKD
VQALWTNDHALAWHLSDDFREDPVAWARTQCQAWEELEDQLPNFLEE
LPDCPCTLTQARADSGRFFTDYGCDMEQGSVCTYHPGAVHCVRSVQA
SLRYGSGQQCCYTADGTQLLTADSSGGSTPDRGHDWGAPPFRTPPRV
PSMSHWLYDVLSFYYCCLWAPDCPRYMQRRPSNDCRNYRPPRLASAF
GDPHFVTFDGTNFTFNGRGEYVLLEAALTDLRVQARAQPGTMSNGTE
TRGTGLTAVAVQEGNSDVVEVRLANRTGGLEVLLNQEVLSFTEQSWM
DLKGMFLSVAAGDRVSIMLASGAGLEVSVQGPFLSVSVLLPEKFLTH
THGLLGTLNNDPTDDFTLHSGRVLPPGTSPQELFLFGANWTVHNASS
LLTYDSWFLVHNFLYQPKHDPTFEPLFPSETTLNPSLAQEAAKLCGD
DHFCNFDVAATGSLSTGTATRVAHQLHQRRMQSLQPVVSCGWLAPPP
NGQKEGNRYLAGSTIYFHCDNGYSLAGAETSTCQADGTWSSPTPKCQ
PGRSYA

CST2
(SEQ ID NO: 20)
WSPQEEDRIIEGGIYDADLNDERVQRALHFVISEYNKATEDEYYRRL
LRVLRAREQIVGGVNYFFDIEVGRTICTKSQPNLDTCAFHEQPELQK
KQLCSFQIYEVPWEDRMSLVNSRCQEA

In a further embodiment, the antibody detection marker is a protein, such as those disclosed above, that is in its native form. As disclosed in the accompanying examples, the inventors utilized a eukaryotic expression system to generate conformation-carrying tumor antigens that are properly folded and contain non-continuous epitopes for use in the detection of autoantibodies. The protein may be used in any suitable format; in one non-limiting embodiment, the protein may be an Fc fusion protein.

In all of the above embodiments, the antibody detection reagents can be labeled with a detectable label. In one embodiment, the detectable labels for reagents to detect autoantibodies against one protein are distinguishable from the detectable labels to detect autoantibodies against the other protein. Methods for detecting the label include, but are not limited to spectroscopic, photochemical, biochemical, immunochemical, physical or chemical techniques. Any suitable detectable label can be used.

The compositions can be stored frozen, in lyophilized form, or as a solution. In one embodiment, the compositions can be placed on a solid support, such as in a microarray or microplate format; this embodiment facilitates use of the compositions in various detection assays. For example, anti-IgG can be used to precoat the wells of a microwell plate and the antibody detection reagents (such as the proteins discussed herein) can be added to the precoated wells.

In a second aspect, the present invention provides methods for detecting breast cancer or breast cancer recurrence, comprising contacting a bodily fluid sample from a subject at risk of having breast cancer or breast cancer recurrence with one or more reagents for detecting autoantibodies against one or more of human ANGPTL4, DKK1, EPHA2, LAMC2, SPON2, SSR2, GAL1, GFRA1, LRRC15, CD147, CD320, CDH3, LRP10, SPINT2, SUSD2, and CST2, wherein the presence of autoantibodies against the one or more proteins correlates with a likelihood of the subject having breast cancer or breast cancer recurrence.

In one embodiment, the composition includes reagents for detecting human autoantibodies against at least two proteins selected from the group consisting of human ANGPTL4, DKK1, EPHA2, GAL1, LAMC2, SPON2, CST2, SPINT2 and SSR2.

As will be understood by those of skill in the art, the methods may include the use of additional antibody detection markers and controls as is appropriate for an intended use of the composition. In one non-limiting embodiment, the compositions may further comprise reagents for detecting antibodies against one or both of mucin-1(MUC1), HER-2 (41), IGFBP2, and GRANULIN.

In another embodiment of the methods of the invention, the compositions comprise or consist of reagents for detecting human autoantibodies against one of the following marker sets:
ANGPTL4, DKK1, GAL1, GFRA1, GRANULIN, LRRC15, and MUC1;
ANGPTL4, DKK1, GAL1, GRANULIN, LRRC15, and MUC1;
ANGPTL4, DKK1, GAL1, and LRRC15;
ANGPTL4, DKK1, GAL1, GFRA1, and LRRC15;
DKK1, GAL1, GFRA1, GRANULIN, LRRC1, and 5 MUC1;
ANGPTL4, DKK1, GAL1, GFRA1, GRANULIN, and LRRC15;
DKK1, GAL1, GRANULIN, LRRC15, and MUC1;
DKK1, GAL1, GFRA1, GRANULIN, and LRRC15;
DKK1, GAL1, GFRA1, LRRC15, and MUC1;
ANGPTL4, DKK1, GAL1, GRANULIN, and LRRC15;
DKK1, GAL1, GFRA1, and LRRC15;
DKK1, GAL1, GRANULIN, and LRRC15;
ANGPTL4, DKK1, GAL1, LRRC15, and MUC1;
DKK1, GAL1, and LRRC15;
ANGPTL4, GAL1, LRRC15, and MUC1;
GAL1, GFRA1, LRRC15, and MUC1;
GAL1, GFRA1, and LRRC15;
ANGPTL4, GAL1, and LRRC15;
DKK1, GAL1, LRRC15, and MUC1;
ANGPTL4, GAL1, GFRA1, and LRRC15;
GAL1, LRRC15, and MUC1;
ANGPTL4, GAL1, GFRA1, LRRC15, and MUC1;
ANGPTL4, GAL1, and GFRA1;
DKK1, GAL1, and GFRA1; and
GAL1, GFRA1, and MUC1.

In another embodiment, the compositions comprise or consist of reagents for detecting human autoantibodies against ANGPTL4, DKK1, GAL1, MUC1, GFRA1, GRN and LRRC15.

The antibody detection markers may be any suitable reagents that can be used to detect antibodies against the recited proteins, including but not limited to the recited protein, a secreted version of the protein (such as a native secreted form of the protein), or an extracellular domain of the protein. Secreted proteins are more easily delivered from tumor cells to lymph nodes, where interactions of immune cells take place resulting in abundant high-affinity antibodies. Membrane surface proteins are commonly released in a soluble form from tumor cells through metalloproteinase-dependent cleavage. The shed proteins are more easily transferred to the lymph nodes than intracellular protein. Thus, in one embodiment the antibody detection marker is a secreted or membrane portion of the recited protein. Exemplary amino acid sequences of the secreted or membrane portion of the recited proteins are as disclosed herein.

In another embodiment, the antibody detection marker comprises or consists of a composition of the invention.

The contacting can be carried out under any suitable conditions for promoting binding between the autoantibodies in the bodily fluid sample and the reagent to forma binding complex that can be detected. Appropriate such conditions can be determined by those of skill in the art based on the intended assay, in light of the teachings herein. Similarly, any suitable additional steps can be used in the methods, such as one or more wash or other steps to remove unbound reagents.

Any suitable detection technique can be used, including but not limited to enzyme linked immunosorbent assays (ELISA), bead based assay platforms such as the Luminex systems, 2-D array based assay platforms such as Search-Light®, and the Inanovate® 'Longitudinal Assay Screening' platform which may be capable of quantitating all the listed breast cancer biomarker from patient samples at their clinically relevant concentrations in a single test and dilution. In one embodiment, the compositions can be placed on a solid support, such as in a microarray, glass slide, membrane, microplate format or beads. The embodiment facilitates use of the compositions. Exemplary such assays are provided in the examples.

Similarly, any suitable bodily fluid can be used, including but not limited to a serum sample, plasma sample or blood sample from the subject. The subject may be any subject at risk of breast cancer, such as a human subject.

In a further embodiment, method identifies the subject as likely to have breast cancer, and wherein the method further comprises treating the subject with an amount of a therapeutic sufficient to treat the breast cancer.

In one non-limiting embodiment of any of the above embodiments, ANGPTL4, DKK1, GAL1, and MUC1 autoantibody response are correlated with BCa; and autoantibody responses against GFRA1, GRN and LRRC15 are inversely correlated with BCa.

In one specific embodiment, the reagents include ANGPTL4, DKK1, GAL1, MUC1, GFRA1, GRN and LRRC15; where, autoantibody responses against GFRA1, GRN and LRRC15 are inversely correlated with BCa. As detailed in the examples, when the autoantibody responses against the 7 antigens were added to the base model, including age, body mass index (BMI), race and current smoking status, the assay had the following diagnostic capabilities: c-stat (95% CI), 0.82 (0.78 to 0.86); sensitivity, 73%; specificity, 76%; and PLR (95% CI), 3.04 (2.34 to 3.94). The model was calibrated across risk deciles (Hosmer-Lemeshow, p=0.13) and performed well in specific subtypes of BCa including estrogen receptor positive, HER-2 positive, invasive, in situ and tumor sizes >1 cm. Diagnostic capabilities of other exemplary marker sets are provided in Table 5.

In a third aspect, the invention provides methods for treating a subject with breast cancer, comprising:
  (a) testing a bodily fluid sample from a subject at risk of breast cancer, and identifying candidate subjects that:
    (i) have autoantibodies against at least one of ANGPTL4, DKK1, GAL1, MUC1, GFRA1, GRN and LRRC15; and/or
    (b) do not have autoantibodies against GFRA1, GRN and/or LRRC15; and
  (b) treating the candidate subjects with an amount of a therapeutic sufficient to treat the breast cancer.

EXAMPLE 1

Breast cancer (BCa) patients elicit an autoantibody response against cancer proteins, which reflects and amplifies the cellular changes associated with tumorigenesis. Detection of autoantibodies in plasma may provide a minimally invasive mechanism for early detection of BCa. To identify cancer proteins that elicit a humoral response, we generated a cDNA library enriched for BCa genes that encode membrane and secreted proteins, which are more likely to induce an antibody response compared to intracellular proteins. To generate conformation-carrying antigens that are efficiently recognized by patients' antibodies, a eukaryotic expression strategy was established. Plasma from 200 BCa patients and 200 age-matched healthy controls were measured for autoantibody activity against 20 different antigens designed to have conformational epitopes using ELISA. A conditional logistic regression model was used to select a combination of autoantibody responses against the 20 different antigens to classify BCa patients from healthy controls. The best combination included ANGPTL4, DKK1, GAL1, MUC1, GFRA1, GRN and LRRC15; however, autoantibody responses against GFRA1, GRN and LRRC15 were inversely correlated with BCa. When the autoantibody responses against the 7 antigens were added to the base model, including age, BMI, race and current smoking status, the assay had the following diagnostic capabilities: c-stat (95% CI), 0.82 (0.78 to 0.86); sensitivity, 73%; specificity, 76%; and PLR (95% CI), 3.04 (2.34 to 3.94). The model was calibrated across risk deciles (Hosmer-Lemeshow, p=0.13) and performed well in specific subtypes of BCa including estrogen receptor positive, HER-2 positive, invasive, in situ and tumor sizes >1 cm.

Introduction

For patients with breast cancer (BCa), early and personalized diagnosis is crucial for optimizing treatments leading to long-term survival. Although mammography is the most widely used method to detect BCa, approximately 20% of screening mammograms result in a false negative diagnosis largely due to high breast density (1). Additionally, 1 in 10 women who get a mammogram will need additional imaging (2). Yet, the overwhelming majority of these women will not have BCa, as only 2 to 4 of every 1,000 screening mammograms leads to a cancer diagnosis (3). Therefore, there is an urgent clinical need to develop a novel, minimally invasive diagnostic strategy for the early diagnosis of BCa.

At present, there is no established tumor marker that is secreted into the peripheral circulation that can be measured by a blood test for the diagnosis of BCa. Currently, tumor markers that are accepted in clinical practice are tissue-based prognostic markers, such as the estrogen receptor (ER), HER-2 amplification, 21-gene Oncotype DX and 70-gene MammaPrint (6-12). All require an invasive biopsy or surgical procedure to acquire tumor tissue for assessment, bearing a heavy burden on patients. Serum tumor markers are valuable tools that allow minimally invasive procedures for sampling to promote the early diagnosis of cancer as well as following the prognosis after treatment (4, 5). However, tumor markers produced by tumor cells usually have relatively low concentrations in the peripheral circulation, especially in early stage disease.

Here we report the use of a molecular approach to identify tumor antigen candidates that elicit an antibody response in BCa patients. Previously, we generated a BCa cDNA library from membrane-associated polyribosomal (MAP) RNA, which encodes secreted and membrane proteins, and subtracted the library with RNA from normal tissues (29). Secreted proteins are more easily delivered from tumor cells to lymph nodes, where interactions of immune cells take place resulting in abundant high-affinity antibodies. Membrane surface proteins are commonly released in a soluble form from tumor cells through metalloproteinase-dependent cleavage. The shed proteins are more easily transferred to the lymph nodes than intracellular proteins (30, 31). Consequently, the obtained subtracted library, referred to as the membrane-associated polyribosomal cDNA library (MAPcL), is enriched with clones encoding membrane and secreted TAA that are highly abundant in BCa and should preferentially induce an antibody response in patients (29). In addition, we have established a method for producing recombinant antigens as Fc fusion proteins designed to have native conformations, which is essential for the expression of membrane and secreted proteins that may induce an antibody response in patients.

We have developed a conformation-carrying antigen ELISA-based strategy to discriminate between BCa and healthy patients by the detection of autoantibodies against a panel of TAAs. Twenty antigens were selected from the most abundant genes represented in the MAPcL, and Fc fusion proteins were generated. Blood was collected from 200 newly diagnosed BCa patients and 200 healthy women as age-matched controls. The 400 plasma samples were screened for the presence of autoantibodies against the 20 different MAPcL-derived antigens using ELISA. A combination of seven antigens with patient demographics yielded the best positive likelihood ratio to discriminate between healthy and BCa patients.

Materials and Methods

Plasmid Construction

For production of MAPcL-rabbit Fc-tagged antigens, two constructs, pSecTag2 (Invitrogen, Carlsbad, Calif.) and pFUSE-rIgG-Fc1 (InvivoGen, San Diego, Calif.), were both utilized to generate the 20 MAPcL-rFc expression constructs because of restriction site availability for cloning. pSecTag2 was modified by amplifying the Fc portion of rabbit IgG using primers 5'-CCG<u>GATATC</u>AGCAAGCCCACGTGCCCACC-3' (SEQ ID NO: 21)
and 5'-AAGGAAAAAA<u>GCGGCCGC</u>TC-ATTTACCCGGAGAGCGGGAG-3' (SEQ ID NO: 22)

(Integrated DNA Technologies, Coralville, Iowa) using pFUSE-rIgG-Fc1 as a template. The rFc PCR product was digested with EcoRV and NotI and inserted into pSecTag2, referred to as pSecTag2-rFc, which contains an IgK signal sequence for secretion. The pFUSE-rIgG-Fc1 contains an IL2 signal sequence. To keep the signal sequence consistent between the two plasmids, the IgK leader sequence was amplified via PCR using pSecTag2 as a template. The IL2 leader sequence was then replaced with the IgK signal sequence, creating pFUSE-IgK-rFc.

The accession numbers of the 20 MAPcL genes used as templates for cloning and predicted signal sequences are indicated in Table 1. The signal sequences of each encoded protein were determined using SignalP (32, 33). If a protein contained a transmembrane domain, only the encoded extracellular portion was included. The transmembrane domains were predicted using the TMHMM database (34). The amino acid numbers encoded by the cloned fragment are shown in Table 1. ANGPTL4, CDH3, DKK1, SPON2, SSR2, CST2, GFRA1 and GAL1 were custom cloned into pSecTag2-rFc using the SfiI and KpnI restriction sites (Genscript, Piscataway, N.J.). EPHA2, IGFBP2 and LAMC2 were custom cloned into pSecTag2-rFc using the KpnI and BamHI restriction sites. GRN, MUC1 and LRRC15 were custom cloned into pSecTag2-rFc using the SfiI and BamHI restriction sites. HER-2, LRP10, SPINT2 and SUSD2 were cloned into pFUSE-IgK-rFc using the SfiI and XhoI restriction sites. CD147 was cloned into pFUSE-IgK-rFc using the BamHI and SacII restriction sites. CD320 was cloned into pFUSE-IgK-rFc using the EcoRI and XhoI restriction sites.

For production of His-tagged HER-2, HER-2 was amplified via PCR using primers 5'-CCCAAGCTTGCAGCACCCAAGTGTGCACCGGCAC-3' (SEQ ID NO: 23) and 5'-GTGCTCGAGTCACGTC-AGAGGGCTGGCTCTCTGCTCG-3'(SEQ ID NO: 24). The product was digested with HindIII and XhoI and cloned directionally into the pET-28a expression vector.

Cell Culture 293T and SKBR3 cell lines were cultured in DMEM with 10% FBS. Cultures were maintained at 37° C. with 5% $CO_2$ in a humidified incubator. All cell lines were authenticated and tested negatively for mycoplasma.

Protein Production

The MAPcL-rFc fusion proteins were produced in 293T cells. Briefly, 293T cells were transfected using Effectene (Qiagen, Valencia, Calif.) according to manufacturer's specifications. During transfection, the cells were cultured in DMEM with 2% FBS. Supernatants containing the secreted fusion proteins were harvested, centrifuged to clear cell debris and supplemented with 0.1% sodium azide. His-HER-2 was produced in *E. coli* BL21 (Invitrogen, Carlsbad, Calif.) and purified using IMAC affinity chromatography.

Sandwich ELISA

Microtiter plates (Nalge Nunc, Rochester, N.Y.) were coated overnight with 2 µg/ml goat anti-rabbit Fc (Jackson Immunoresearch, West Grove, Pa.) diluted with phosphate buffered saline. The supernatants containing the rFc fusion proteins were diluted 1:3 serially in standard blocking buffer (0.5% bovine serum albumin and 0.1% sodium azide in phosphate buffered saline). Plates were washed once, and the serially diluted supernatants were transferred to the microtiter plates. Rabbit IgG of known concentration was diluted similarly and added to one row of the microtiter plate

TABLE 1

MAPcL Candidates for Generation of rFc Fusion Proteins

| Gene from MAPcL | Accession # | Signal Sequence* Amino Acids | Encoded Amino Acid Fragment† |
|---|---|---|---|
| ANGPTL4 (angiopoietin-like 4) | NM_139314 | 1-30 | 31-406 |
| CD147 | NM_198589 | 1-21 | 22-162 |
| CD320 | NM_016579 | 1-46 | 47-230 |
| CDH3 (cadherin 3) | NM_001793 | 1-24 | 25-654 |
| CST2 (cystatin SA) | NM_001322 | 1-20 | 21-141 |
| DKK1 (dickkopf WNT signaling pathway inhibitor 1) | NM_012242 | 1-28 | 29-266 |
| EPHA2 (EPH receptor A2) | NM_004431 | 1-26 | 27-535 |
| GAL1 (lectin, galactoside-binding, soluble, 1) | NM_002305 | 1-17 | 18-135 |
| GFRA1 (GPI-linked anchor protein) | AF038421 | 1-24 | 25-465 |
| GRN (granulin) | NM_002087 | 1-17 | 18-593 |
| HER-2 | NM_004448 | 1-22 | 23-652 |
| IGFBP2 (insulin-like growth factor binding protein 2) | NM_000597 | 1-39 | 40-328 |
| LAMC2 (laminin, gamma 2) | NM_005562 | 1-21 | 22-1111 |
| LRP10 (low density lipoprotein receptor-related protein 10) | NM_014045 | 1-16 | 17-440 |
| LRRC15 (leucine rich repeat containing 15) | NM_001135057 | 1-27 | 28-544 |
| MUC1 (mucin 1) | NM_002456 | 1-22 | 23-167 |
| SPINT2 (serine peptidase inhibitor, Kunitz type, 2) | NM_021102 | 1-27 | 28-198 |
| SPON2 (sporadin 2) | NM_012445 | 1-26 | 27-331 |
| SSR2 (signal sequence receptor, beta (translocon-associated protein beta)) | NM_003145 | 1-17 | 18-146 |
| SUSD2 (sushi domain containing 2) | NM_019601 | 1-27 | 28-785 |

*The signal sequences of each encoded protein were determined using SignalP (32, 33) and were not included in the expression constructs.
†The amino acid numbers indicate the encoded portion of the proteins cloned between the Ig signal sequence and the Fc portion of rabbit IgG to generate the secreted MAPcL-rFc fusion proteins.

in order to quantify the amount of fusion protein present in the culture media. After incubating for two hours, plates were washed twice and 50 μl of HRP-conjugated goat anti-rabbit IgG (Jackson Immunoresearch, West Grove, Pa.) diluted 1:3000 in standard blocking buffer with 0.05% Tween 20 added. After a 2-hour incubation, plates were washed 4 times and developed with 100 μl/well of TMB substrate (Pierce, Rockford, Ill.). The development reaction was stopped after five minutes with 50 μl/well of 2N $H_2SO_4$, and the absorbance was measured at 450 nm to determine the concentration. The absorbance at 690 nm was subtracted to remove background signal.

Antibody Recognition of Conformational Versus Denatured HER-2 Protein

For the conformational HER-2 assay, microtiter plates were coated with 2 μg/ml goat anti-rabbit Fc (Jackson Immunoresearch, West Grove, Pa.) in PBS overnight. HER-2-ECD-rFc was then added to each well, 100 μl/well. For denatured HER-2, microtiter plates were coated with 2 μg/ml His-HER-2-ECD in PBS overnight.

Three HER-2 antibodies were used in the assay: anti-HER-2 3F27 (US Biological, Swampscott, Mass.), anti-HER-2 3F32 (US Biological, Swampscott, Mass.) and Herceptin (Genentech, South San Francisco, Calif.). Each antibody was diluted to 1 μg/ml in standard blocking buffer with 0.05% Tween 20. The antibodies were then serially diluted. After washing once, 50 μl/well of the serially diluted antibodies was added to the plates and incubated for 2 hours at room temperature. The plates were washed three times, and species appropriate HRP-conjugated secondary antibodies were added at a 1:3000 dilution. Plates were washed four times and developed with 100 μl/well TMB substrate for five minutes. Development was stopped with 50 μl/well 2N $H_2SO_4$. Absorbance was measured at 450 nm, and the 690 nm absorbance was subtracted to account for background.

The same antibodies were used to stain HER-2 in SKBR3 BCa cells via flow cytometry. SKBR3 cells were detached from dish using Cell Dissociation Solution Non-enzymatic 1× (Sigma, St. Louis, Mo., catalog # C5914). $2 \times 10^5$ cells were incubated with 0.5 μg/ml of each antibody for 1 hour at room temperature. The cells were then washed, and a 1:200 dilution of PE-conjugated antibody for the appropriate species was added. The cells were again washed, resuspended in FACS buffer (PBS with 5% bovine serum albumin and 0.1% sodium azide) and analyzed by flow cytometry.

Competition of Herceptin Binding

Microtiter plates were coated with 4 μg/ml goat anti-rabbit Fc and incubated overnight. After one wash, 100 μl/well HER-2-ECD-rFc was added to each well and incubated overnight. HER-2-Fc and CD30-Fc chimeric proteins (R&D Systems, Minneapolis, Minn.) were serially diluted from a starting concentration of 10 ug/ml. Herceptin was added to a final concentration of 10 ng/ml in each of the serial chimeric protein dilutions. Plates were washed twice, and 50 μl/well of chimeric protein/Herceptin mixture was applied to the plate. Plates were then washed three times, and a 1:3000 dilution of HRP goat anti-human IgG was applied to each well, 50 μl/well. After four washes, 100 μl/well TMB substrate was added to each well. Development was stopped with 50 μl/well 2N H2SO4 after 5 minutes. Absorbance was measured at 450 nm with 690 nm absorbance subtracted.

Patients

The inclusion criteria for cases were women over 30 years of age that were newly diagnosed with BCa (any type) at Sanford Health, Sioux Falls, S. Dak. Patients were asked to provide one extra 10 ml EDTA tube of blood prior to mastectomy, lumpectomy, radiation therapy, chemotherapy or other treatment. Case subjects were excluded only if they had a previous history of cancer of any kind Healthy control subjects had a negative mammogram within six months before the blood draw. Healthy subjects were excluded if there was a history of previous cancer of any kind or a history of autoimmune disease. All patients provided written informed consent, and the Sanford Health IRB approved the study protocol. Blood samples from 200 BCa patients were collected from Oct. 8, 2009 to Apr. 17, 2012. In addition, 200 age-matched healthy control blood samples were collected from Oct. 16, 2009 to Jan. 19, 2011. See Table 2 for enrolled patients' characteristics.

TABLE 2

Patient Clinical and Pathological Characteristics

| Patients with Breast Cancer | N = 200 |
|---|---|
| Age: Mean (SD) | 58.9 (11.4) |
| White Race: n (%) | 193 (97%) |
| BMI [kg/m2]: Mean (SD) | 29.7 (6.6) |
| Smoking Status: n (%) | |
| Current | 22 (11%) |
| Never | 120 (60%) |
| Past | 58 (29%) |
| Family History Yes: n (%) | 114 (58%) |
| Tumor Type: n (%) | |
| Invasive | 148 (74%) |
| in situ | 52 (26%) |
| Histology: n (%) | |
| Ductal and Lobular | 3 (2%) |
| Ductal | 173 (87%) |
| Lobular | 21 (11%) |
| Other | 2 (1%) |
| ER Positive: n (%) | 171 (86%) |
| PR Positive: n (%) | 147 (74%) |
| HER-2 Amplification: n (%) | |
| Negative | 156 (78%) |
| Positive | 33 (17%) |
| Unknown | 11 (6%) |
| Triple Negative Yes: n (%) | 18 (12%) |
| Tumor Max Dimension [cm]: n (%) | |
| ≤1 | 66 (36%) |
| >1 to ≤2 | 65 (35%) |
| >2 | 53 (29%) |
| Lymph Node Involvement: n (%) | 47 (24%) |
| Age-Matched Controls with Negative Mammogram | N = 200 |
| Age: Mean (SD) | 58.8 (11.3) |
| White Race: n (%) | 192 (97%) |
| BMI [kg/m2]: Mean (SD) | 27.1 (5.5) |
| Smoking Status: n (%) | |
| Current | 7 (4%) |
| Never | 125 (63%) |
| Past | 67 (34%) |

Serum Collection

Blood was collected in a 10 ml EDTA tube and centrifuged at 2000×g for 10 minutes. Plasma was removed from the tube, aliquoted and stored at −80 degrees Celsius until screening for the presence of autoantibodies.

Conformation-Carrying Antigen ELISA

Microtiter plates (Nalge Nunc, Rochester, N.Y.) were coated overnight with 4 μg/ml goat anti-rabbit Fc (Jackson Immunoresearch, West Grove, Pa.) in phosphate buffered saline. Plates were washed once, and 100 μl/well of MAPcLrFc fusion protein was added. Plates were incubated for 2 hours and washed twice. The plates were then coated with 50 µl/well of optimized blocking buffer (phosphate buffered saline with 0.5% bovine serum albumin, 0.2% dry milk, 0.1% polyvinylpyrrolidone, 20 mM L-Glutamine, 20 mM L-Arginine, 0.1% sodium azide, 10% goat serum, and 0.05% Tween 20). The plates were incubated for 1 hour at 37° C. and washed once. Serum samples diluted 1:100 in optimized blocking buffer were added and incubated for 2 hours at room temperature. Plates were then washed three times, and autoantibodies were detected using an HRP-conjugated goat anti-human IgG (Jackson Immunoresearch, West Grove, Pa.) diluted 1:3000 in standard blocking buffer with 0.05% Tween 20. Plates were incubated for 1 hour at room temperature, washed four times and developed with 100 µl/well of TMB substrate (Pierce, Rockford, Ill.) for 15 minutes. Development was stopped with 50 µl/well 2N $H_2SO_4$, and the absorbance was measured at 450 nm. The absorbance at 690 nm was subtracted to remove background signal. Each 96-well plate included 14 samples from BCa subjects and 14 samples from normal mammogram subjects. Each sample was tested in triplicate within the same plate. One row in each plate was subjected only to blocking buffer as a negative control for the ELISA.

Statistical Methods

Controls were individually matched to 200 BCa patients 1:1 within a 3-year age window using a greedy caliper matching algorithm (35) while blinded to assay data. For each subject the antigen level was transformed by subtracting the mean of the blocking buffer from the mean of the triplicate measurements. If the difference was less than zero, it was set to zero, and the square root was taken to yield a more symmetrical distribution.

Differences in demographics and autoantibody responses between BCa patients and controls were tested using two-sample t-test and Chi-squared test for continuous and categorical data, respectively. The incremental improvement to the c-statistic (i.e. concordance index, area under the receiver operating characteristic (ROC) curve) was tested by adding the autoantibody response to each antigen to a logistic regression model that already included age, BMI, race, and current smoking status. The model calibration was tested using the Hosmer-Lemeshow goodness-of-fit measure, which constructs a Chi-squared statistic by comparing the predicted and observed number of cases by probability decile (36).

After assessing the individual antigens, a multivariable conditional logistic regression analysis with strata for age-matching was used to determine the subset of antigens that minimized Akaike's Information Criterion (37); all models were adjusted for BMI, race, and current smoking status. Exploratory subgroup analyses were performed to determine if the multivariable subset of antigens performed differently in a particular type of BCa. The multivariable model was tested in the following subgroups: invasive, in situ, ER positive, tumor maximum dimension >1 cm, lymph node involvement, and HER-2 positive. The critical level alpha was set to ≤0.05/20 antigens=0.0025 using the Bonferroni correction. SAS® (Cary, N.C.) version 9.3 software was used for all analyses.

Results

Generation of Tumor-associated Antigens Designed to have Native Conformations

To identify TAAs that elicit a humoral response in patients, candidate genes that encode membrane and secreted proteins were selected from the most abundant genes represented in the MAPcL. Because only 10% of epitopes on proteins are in a linear continuous sequence (24), we utilized a eukaryotic expression system to generate conformation-carrying tumor antigens that are properly folded and contain noncontinuous epitopes for use in the detection of autoantibodies. Sequences encoding the extracellular domains (ECD) or the secreted proteins without the signal sequence of the candidate MAPcL genes were cloned 5' of the Fc region of rabbit IgG (rFc) into the pSecTag2-rFc vector or pFUSE-IgK-rFc, depending on restriction enzyme cloning sites. The IgK leader sequence contained in the vectors directs the fusion proteins to be secreted. The vectors encoding the fusion proteins were transiently transfected into 293T cells, and the corresponding fusion proteins were secreted into the media. Production of the secreted fusion proteins was confirmed using a sandwich ELISA, and the concentrations were determined by comparison to an established CD147-rFc standard (data not shown).

To demonstrate that the generated MAPcL-rFc proteins were designed to be folded into a native conformation, an ELISA analysis was performed using commercially available anti-HER-2 antibodies generated against either native (monoclonal antibody 3F32 and Herceptin) or denatured (monoclonal antibody 3F27) HER-2 protein. Two antigens consisting of the ECD of HER-2 were analyzed: the conformation-carrying HER-2-ECD-rFc protein generated in 293T cells and a His-HER-2-ECD protein that was produced in bacteria and purified over a nickel column. The anti-native HER-2 antibody (3F32) recognized the HER-2-ECD-rFc produced in 293T (FIG. 1A), but was unable to detect the purified His-HER-2-ECD protein produced in bacteria (FIG. 1B). Also, Herceptin was unable to detect the denatured His-HER-2-ECD protein purified from bacteria (FIG. 1B). However, a strong response was observed for Herceptin when HER-2-ECD-rFc protein was used as the antigen for the ELISA analysis (FIG. 1A). Although the 3F27 antibody generated against denatured HER-2 did not detect the HER-2-ECD-rFc protein (FIG. 1A), this antibody had a strong response to bacterial HER-2-ECD (FIG. 1B).

To confirm the specific recognition of native versus denatured epitopes by the purchased antibodies, flow cytometry was performed on unfixed SKBR3 cells, a BCa cell line known to have HER-2 amplification (38). Because surface HER-2 would retain its native confirmation on the unfixed SKBR3 cells, the anti-HER-2 3F27 antibody, specific for denatured HER-2, was unable to detect surface HER-2 on the cell membrane of SKBR3 cells by flow cytometry (FIG. 1C). When anti-HER-2 3F32 antibody and Herceptin, both of which recognize conformational HER-2, were used for flow cytometry analysis, a large shift in fluorescence was observed indicated that the antibodies recognized HER-2 present on the membrane of the SKBR3 cells (FIG. 1C).

A binding competition assay was performed to verify that the conformation-carrying antigen ELISA was recognizing the MAPcL antigen specifically. Wells were precoated with anti-rabbit IgG followed by HER-2-ECD-rFc. Purchased HER-2-Fc and CD30-Fc purified chimeric proteins (R&D Systems) were serially diluted and added to a constant amount of Herceptin (10 ng/ml) in each well. Following the addition of the HRP-conjugated secondary anti-human IgG antibody, the reactions were developed. Herceptin binding to HER-2-ECD-rFc was competed by addition of HER-2-Fc but not the CD30-Fc protein (FIG. 1D). This result indicates that Herceptin is binding specifically to the HER-2-ECD portion of the conformation-carrying fusion protein.

Screening of Patients for Autoantibodies Using the Conformation-carrying Antigen ELISA Twenty MAPcL-rFc fusion antigens designed to contain their native conformation were generated by cloning the sequences encoding the ECD or secreted proteins 5' of the rFc sequence (see Table 1 for identity of all 20 antigens). The expression plasmids were individually transfected into 293T cells, and the MAPcL-rFc fusion proteins were secreted into the media. The 20 fusion proteins were quantitated by sandwich ELISA analysis (data not shown). To detect autoantibodies in plasma collected from patients, a conformation-carrying antigen ELISA was developed using the generated MAPcL-rFc antigens. To immobilize the MAPcL-rFc fusion proteins, anti-rabbit IgG was used to precoat the wells of a 96-well plate. The media from the transfected 293T cells, which contains the generated MAPcL-rFc fusion proteins designed to have native conformations, was added to the precoated wells. To reduce plate variation and increase repeatability of the assay, three replicate samples using the plasma from each individual patient were distributed across the 96-well plate. After addition of an HRP-conjugated secondary anti-human IgG antibody, the plates were developed and the absorbance of each well was measured. The 200 plasma samples collected from newly diagnosed BCa patients and plasma from 200 age-matched healthy subjects were evaluated for autoantibody reactivity against the 20 antigens using the conformation-carrying ELISA.

The 200 BCa patients and 200 healthy controls had a mean (SD) age of 59 (11) years and 97% self identified as white race (Table 2). Cancer patients were more overweight (29.7 vs. 27.1 kg/m$^2$, p<0.0001) and had different smoking habits (p=0.014), such that there was a greater prevalence of current smokers (11% vs. 4%) in the cancer subjects versus healthy. The 200 BCa patients represented the heterogeneity of the disease consisting of 74% invasive, 24% lymph node involvement, 86% ER-positive, 17% HER-2 positive and 12% triple negative BCa (Table 2). Analyzing the absorbance reading of the autoantibody responses against the individual antigens, we determined that there were significant Bonferroni adjusted differences between BCa patients and controls in autoantibody responses against 12 TAAs, i.e. ANGPTL4, DKK1, EPHA2, GAL1, HER-2, IGFBP2, LAMC2, MUC1, SPON2, CST2, SPINT2 and SSR2 (Table 3). Higher levels of these autoantibodies were detected in BCa patients. In logistic regression models adjusted for age, race, BMI and current smoking status, autoantibody responses against MUC1 (1.83), DKK1 (1.77) and GAL1 (1.75) (all p<0.0001) had the largest odds ratios (OR), such that a patient was about 1.8 times as likely to have BCa per 1 SD increase in autoantibody response against any of these three antigens (Table 3). Autoantibody responses against six of the twelve antigens (i.e. GAL1, DKK1, MUC1, ANGPTL4, EPHA2 and IGFBP2) also increased the area under the ROC curve when each of them was added individually to the base logistic regression model adjusted for age, BMI, race and current smoking status (all p<0.05). Five of the six models were well calibrated across probability deciles (minimum Hosmer-Lemeshow p=0.13), but the model including IGFBP2 was not calibrated (p=0.016).

TABLE 3

Absorbance Measurements of Autoantibodies and their Association with Breast Cancer

| Autoantibody | Normal Mammogram (n = 200) | Breast Cancer (n = 200) | P-value* | Odds Ratio† | 95% CI | Increase in c-statistic‡ | P-value |
|---|---|---|---|---|---|---|---|
| CD320 | 0.15 (0.12) | 0.16 (0.12) | 0.62 | 1.10 | 0.90-1.35 | 0.000 | 0.96 |
| EPHA2 | 0.13 (0.06) | 0.16 (0.10) | 0.0006 | 1.64 | 1.21-2.24 | 0.034 | 0.037 |
| GFRA1 | 0.18 (0.06) | 0.20 (0.08) | 0.0081 | 1.28 | 1.03-1.59 | 0.013 | 0.32 |
| IGFBP2 | 0.21 (0.12) | 0.25 (0.13) | 0.0006 | 1.39 | 1.10-1.75 | 0.030 | 0.050 |
| CST2 | 0.17 (0.09) | 0.20 (0.10) | 0.0013 | 1.39 | 1.12-1.73 | 0.026 | 0.13 |
| GAL1 | 0.17 (0.06) | 0.20 (0.07) | <0.0001 | 1.75 | 1.37-2.23 | 0.051 | 0.021 |
| HER-2 | 0.13 (0.04) | 0.15 (0.06) | <0.0001 | 1.65 | 1.28-2.13 | 0.039 | 0.054 |
| LAMC2 | 0.15 (0.05) | 0.17 (0.08) | 0.0007 | 1.47 | 1.16-1.88 | 0.025 | 0.13 |
| ANGPTL4 | 0.18 (0.05) | 0.20 (0.06) | 0.0001 | 1.57 | 1.24-1.99 | 0.041 | 0.032 |
| DKK1 | 0.18 (0.10) | 0.24 (0.11) | <0.0001 | 1.77 | 1.40-2.24 | 0.060 | 0.0093 |
| MUC1 | 0.14 (0.06) | 0.18 (0.08) | <0.0001 | 1.83 | 1.41-2.37 | 0.055 | 0.012 |
| SSR2 | 0.14 (0.07) | 0.17 (0.08) | 0.0007 | 1.53 | 1.23-1.92 | 0.029 | 0.14 |
| LRP10 | 0.14 (0.05) | 0.15 (0.07) | 0.0098 | 1.35 | 1.09-1.68 | 0.011 | 0.47 |
| LRRC15 | 0.11 (0.04) | 0.12 (0.05) | 0.30 | 1.09 | 0.89-1.34 | 0.001 | 0.82 |
| SPINT2 | 0.15 (0.07) | 0.18 (0.09) | 0.0022 | 1.40 | 1.13-1.74 | 0.018 | 0.31 |
| SPON2 | 0.14 (0.07) | 0.17 (0.08) | <0.0001 | 1.65 | 1.31-2.07 | 0.042 | 0.052 |
| CD147 | 0.10 (0.05) | 0.12 (0.06) | 0.0039 | 1.43 | 1.15-1.78 | 0.016 | 0.38 |
| CDH3 | 0.10 (0.04) | 0.12 (0.04) | 0.0033 | 1.43 | 1.14-1.79 | 0.014 | 0.40 |
| GRN | 0.12 (0.06) | 0.13 (0.07) | 0.19 | 1.16 | 0.94-1.43 | 0.004 | 0.65 |
| SUSD2 | 0.12 (0.04) | 0.13 (0.05) | 0.0085 | 1.36 | 1.10-1.70 | 0.013 | 0.38 |

Data shown as mean (SD) of $\sqrt{O.D. - Background}$;
*Differences between groups were tested using t-tests;
Significant Bonferroni adjusted p-value <0.05/20 = 0.0025 are shown in bold;
†Odds ratio (95% CI) for breast cancer prevalence per 1 SD increase in autoantibody was determined using logistic regression models adjusted for age, race, BMI and current smoking status;
‡Change in area under the ROC curve (i.e. c-statistic) was determined when autoantibody was added to the adjusted logistic regression models.

Figure 2:
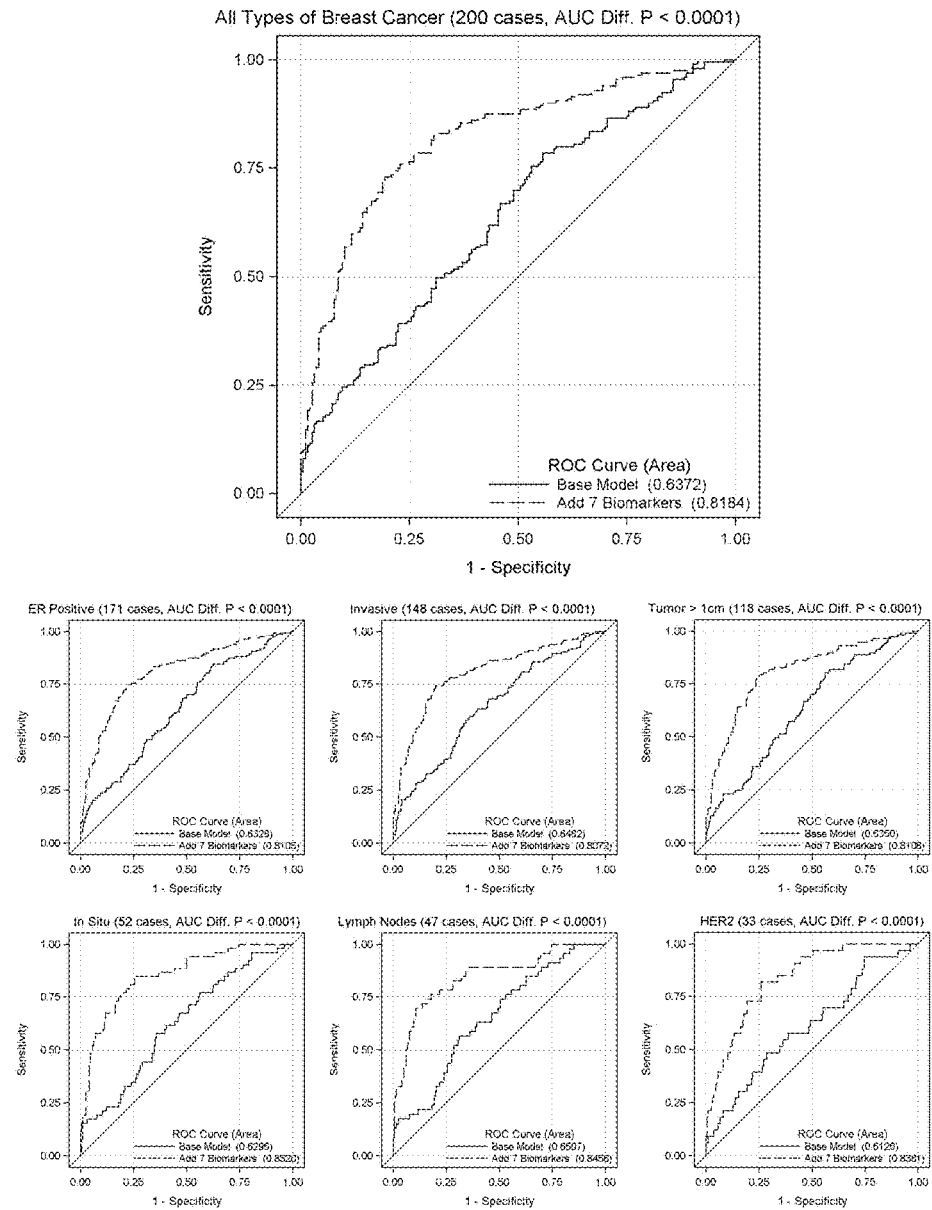
FIG. 2. ROC curve comparison for classification of breast cancer patients. The autoantibody responses against seven antigens (i.e. ANGPTL4, DKK1, GAL1, GFRA1, GRN, LRRC15 and MUC1) were added to a logistic regression model that included age, BMI, race and current smoking status. The ROC curves were determined for all subjects (top) and by specific subtypes of breast cancer including ER positive, invasive, maximum tumor dimension >1 cm, in situ, lymph node involvement and HER-2 amplification (bottom).

To increase the predictive ability of the conformation-carrying ELISA, the autoantibody response against a group of antigens was determined using conditional logistic regression analysis incorporating the individual age-matching study design and adjusting for BMI, race and current smoking status. The group with the best model fit (i.e. minimum AIC) contained the autoantibody responses against the following 7 antigens: ANGPTL4, DKK1, GAL1, MUC1, GFRA1, GRN and LRRC15 (Table 4). Of these 7, only autoantibody responses against ANGPTL4, DKK1, MUC1 and GAL1 individually showed a significant increase in the area under the ROC curve when added to the base model (Table 3). In the fully adjusted logistic regression model including the group of antigens, current smoking had the largest OR (95% CI) of prevalent BCa OR=7.88 (2.68-23.2); and BMI was also a significant risk factor OR=1.09 (1.04-1.13) per 1 kg/m$^2$ increase (Table 4). GAL1 had an OR of 6.73 (3.42-13.3), so a patient was almost 7 times as likely to have BCa per 1 SD increase in autoantibody response against GAL1. The autoantibody responses against GFRA1 (OR=0.41), GRN (OR=0.55) and LRRC15 (OR=0.32) all had inverse associations with odds of prevalent BCa when adjusted for responses against the other antigens (Table 4). Taken together, the autoantibody response against the group of 7 antigens increased the area under the ROC curve from 0.64 to 0.82 (p<0.0001) and had the following diagnostic measures: sensitivity (72.9%), specificity (76.0%), and positive likelihood ratio (95% CI) 3.04 (2.34 to 3.94) (FIG. 2). The model was also calibrated across risk deciles (Hosmer-Lemeshow, p=0.13).

TABLE 4

Multivariable Logistic Regression Model Odds Ratios for Breast Cancer

| Variable | Odds Ratio | 95% | CI |
|---|---|---|---|
| Age (per 1 year) | 1.00* | 0.98 | 1.02 |
| White Race | 0.70 | 0.19 | 2.68 |
| BMI (per 1 kg/m$^2$) | 1.09 | 1.04 | 1.13 |
| Current Smoking | 7.88 | 2.68 | 23.2 |
| ANGPTL4 (per 1 SD) | 1.71 | 1.16 | 2.50 |
| DKK1 (per 1 SD) | 1.87 | 1.28 | 2.73 |
| GAL1 (per 1 SD) | 6.73 | 3.42 | 13.3 |
| GFRA1 (per 1 SD) | 0.41 | 0.21 | 0.82 |
| GRN (per 1 SD) | 0.55 | 0.38 | 0.81 |
| LRRC15 (per 1 SD) | 0.32 | 0.19 | 0.55 |
| MUC1 (per 1 SD) | 1.67 | 1.16 | 2.41 |

*Due to individual 1:1 age-matching.

Because BCa is a heterogeneous disease, it is possible that the autoantibody response against a combination of antigens may categorize a subtype of BCa differently than analyzing all BCa subtypes as a whole. The BCa samples were grouped into individual BCa subtypes: invasive, in situ, ER positive, tumor maximum dimension >1 cm, lymph node involvement and HER-2 positive. The ability to discriminate cases from controls in each subtype was tested using autoantibody reactivity against the 7-antigen combination in addition to age, BMI, race and current smoking status (FIG. 2). The 7-antigen combination model performed similarly in all subtypes of BCa; the c-statistic was 0.81 to 0.85. Of the BCa subtypes, in situ tumors had the greatest area under the ROC curve (0.8520, p<0.0001) when analyzed for autoantibody responses against the 7-antigen combination. The model was not calibrated when considering only those cancers with lymph node involvement due to four unexpected BCas with very low model probabilities (Hosmer-Lemeshow p=0.0036).

Discussion

Early detection of BCa allows a physician to treat the initial stage of the disease before metastasis, thereby allowing for a higher rate of remission or long-term survival for the patient. Detecting the presence of autoantibodies generated against tumor proteins in the blood of patients would be an ideal method for BCa detection. However, the tumor antigens need to be identified before specific autoantibody responses in patients can be ascertained. We generated a library that encodes membrane and secreted proteins that are highly expressed in BCa and may elicit an immune response.

We have shown that antigen conformation alters antibody-binding affinity in our assay, and the detection of autoantibodies is limited by epitope conformation (FIG. 1). We used a robust sample set to develop the conformation-carrying ELISA consisting of 200 plasma samples collected from newly diagnosed BCa patients before surgery, chemotherapy or radiation treatment. In addition, plasma was collected from 200 age-matched subjects defined by a confirmed normal mammogram in the preceding six months (Table 2). All 400 plasma samples were screened individually for autoantibody response against 20 TAAs designed to contain their native conformation using ELISA. Four of the 20 TAAs analyzed in our assay have previously been reported to generate an antibody response in BCa patients: MUC1 (39, 40), HER-2 (41), IGFBP2 (15) and GRN (42). Detection of autoantibodies against 12 of the 20 antigens was statistically significant for discriminating between normal and cancer samples (Table 3, bold). However, we did not observe a significant autoantibody response against GRN in our assay. Of the 12 significant antigens, 9 have not been previously associated with BCa autoantibodies. To our knowledge, this is the first report of the detection of autoantibodies against ANGPTL4, CST2, DKK1, EPHA2, GAL1, LAMC2, SPINT2, SPON2 and SSR2 in BCa patients (Table 3).

Previously it has been shown that screening serum against a panel of antigens to detect autoantibodies compared to only a single antigen increases the sensitivity of the assay (17). This finding is consistent with the fact that BCa is a heterogeneous disease (43), and each individual patient's immune system is distinct. A combination of seven TAAs, consisting of ANGPTL4, DKK1, GAL1, MUC1, GFRA1, GRN and LRRC15, had the greatest diagnostic capability (Table 4). Compared to previously published multiple antigen panels used to detect BCa autoantibodies (17, 44-46), the combination of these seven TAAs is unique, and our study contains the largest patient population of BCa and healthy samples. Interestingly, in the seven-antigen combination, four of the antigens have statistical significance individually (Table 3), but three of the antigens, GFRA1, GRN and LRRC15, were not statistically significant on their own (Table 3). However, GFRA1, GRN and LRRC15 were inversely associated with BCa, indicating that lower amounts of these autoantibodies in a patient, in combination with higher levels of the directly associated autoantibodies, increased the likelihood of having BCa (Table 4). When the 7 antigens were added to knowledge of current smoking status and BMI, the sensitivity and specificity of the assay was 72.9% and 76.0%, respectively. The area under the ROC curve (95% CI) was 0.82 (0.77 to 0.85), and the positive likelihood ratio was 3.04 for the conformation-carrying ELISA. Because BCa is a heterogeneous disease, patients were grouped into tumor characteristics, including ER positive, HER-2 positive, in situ, invasive, tumor size and lymph node involvement. The 7-antigen combination performed well for all groups (FIG. 2). These results suggest that the assay has potential clinical application. One serum recurrence marker for BCa that is currently used in the clinic is mucin-associated antigen CA27.29. The CA27.29 antigen is detected in the blood of a patient using a monoclonal antibody that recognizes MUC1. Because of the low sensitivity of the CA27.29 tumor marker, the test is used to follow a patient for BCa recurrence (47). Compared to the traditional CA27.29 tumor marker, the conformation-carrying ELISA described here shows great promise.

Currently, mammography is the standard method for BCa screening. However, the machinery necessary to perform a mammogram is expensive, requires specialized medical personnel to operate and is challenging to transport to medically underserved areas. The development of a blood test for the early detection of BCa would greatly advance access to screening. Drawing blood is a common procedure, and blood can easily be mailed to a clinical laboratory for analysis. This study demonstrates that a combination of autoantibody responses against antigens designed to contain conformational epitopes is a promising strategy for BCa detection. Future studies will focus on the identification of additional antigens to improve the sensitivity and specificity of the assay for translation into the clinic.

TABLE 5

Autoantibody combination subsets and their association with breast cancer

| Plex | Sets of Autoantibodies | Sensitivity % | Specificity % | PLR | ROC AUC | Increase in ROC AUC* |
|---|---|---|---|---|---|---|
| 7 | ANGPTL4 DKK1 GAL1 GFRA1 GRANULIN LRRC15 MUC1 | 72.9 | 76.0 | 3.04 | 0.818 | 0.181 |
| 6 | ANGPTL4 DKK1 GAL1 GRANULIN LRRC15 MUC1 | 72.4 | 75.5 | 2.96 | 0.810 | 0.173 |
| 4 | ANGPTL4 DKK1 GAL1 LRRC15 | 69.8 | 74.5 | 2.74 | 0.790 | 0.152 |
| 5 | ANGPTL4 DKK1 GAL1 GFRA1 LRRC15 | 69.3 | 74.5 | 2.72 | 0.803 | 0.165 |
| 6 | DKK1 GAL1 GFRA1 GRANULIN LRRC15 MUC1 | 70.4 | 74.0 | 2.71 | 0.809 | 0.172 |
| 6 | ANGPTL4 DKK1 GAL1 GFRA1 GRANULIN LRRC15 | 70.9 | 73.5 | 2.68 | 0.812 | 0.175 |
| 5 | DKK1 GAL1 GRANULIN LRRC15 MUC1 | 69.8 | 73.0 | 2.59 | 0.805 | 0.167 |
| 5 | DKK1 GAL1 GFRA1 GRANULIN LRRC15 | 68.3 | 73.5 | 2.58 | 0.799 | 0.162 |
| 5 | DKK1 GAL1 GFRA1 LRRC15 MUC1 | 68.8 | 73.0 | 2.55 | 0.797 | 0.160 |
| 5 | ANGPTL4 DKK1 GAL1 GRANULIN LRRC15 | 68.3 | 73.0 | 2.53 | 0.804 | 0.166 |
| 4 | DKK1 GAL1 GFRA1 LRRC15 | 68.3 | 73.0 | 2.53 | 0.791 | 0.153 |
| 4 | DKK1 GAL1 GRANULIN LRRC15 | 68.8 | 72.4 | 2.49 | 0.796 | 0.159 |
| 5 | ANGPTL4 DKK1 GAL1 LRRC15 MUC1 | 69.8 | 71.4 | 2.44 | 0.794 | 0.157 |
| 3 | DKK1 GAL1 LRRC15 | 66.8 | 72.4 | 2.42 | 0.784 | 0.147 |
| 4 | ANGPTL4 GAL1 LRRC15 MUC1 | 66.8 | 72.4 | 2.42 | 0.784 | 0.147 |
| 4 | GAL1 GFRA1 LRRC15 MUC1 | 68.3 | 71.4 | 2.39 | 0.788 | 0.151 |
| 3 | GAL1 GFRA1 LRRC15 | 66.8 | 71.9 | 2.38 | 0.770 | 0.132 |
| 3 | ANGPTL4 GAL1 LRRC15 | 71.6 | 69.8 | 2.37 | 0.774 | 0.137 |
| 4 | DKK1 GAL1 LRRC15 MUC1 | 67.8 | 71.4 | 2.37 | 0.789 | 0.152 |
| 4 | ANGPTL4 GAL1 GFRA1 LRRC15 | 68.8 | 70.9 | 2.36 | 0.793 | 0.156 |
| 3 | GAL1 LRRC15 MUC1 | 67.3 | 71.4 | 2.35 | 0.778 | 0.141 |
| 5 | ANGPTL4 GAL1 GFRA1 LRRC15 MUC1 | 68.8 | 69.9 | 2.29 | 0.798 | 0.161 |
| 3 | ANGPTL4 GAL1 GFRA1 | 64.8 | 66.3 | 1.92 | 0.753 | 0.116 |
| 3 | DKK1 GAL1 GFRA1 | 65.3 | 65.8 | 1.91 | 0.746 | 0.109 |
| 3 | GAL1 GFRA1 MUC1 | 63.3 | 64.8 | 1.80 | 0.746 | 0.109 |

PLR = positive likelihood ratio, sensitivity/(100 − specificity);
ROC = receiver operating characteristic curve;
AUC = area under the curve;
*Change in area under the ROC curve (i.e. c-statistic) was determined when the set of autoantibodies was added to a logistic regression model adjusted for age, race, BMI, and current smoking status (all p-value <0.0001).

REFERENCES

1. National Cancer Institute at the National Institutes of Health 2012 [updated Jul. 24, 2012; cited 2013]. Available from: http://www.cancer.gov/cancertopics/factsheet/detection/mammograms.
2. Breastcancer.org, Mammography: Benefits, Risks, What You Need to Know 2013. Available from: http://www.breastcancer.org/symptoms/testing/types/mammograms/benefits_risks.jsp.
3. American Cancer Society, Find Support & Treatment, Mammograms and Other Breast Imaging Procedures 2012. Available from: http://www.cancer.org/Treatment/UnderstandingYour Diagnosis/ExamsandTestDescriptions/MammogramsandOtherBreastImagingProcedures/mammo grams-and-other-breast-imaging-procedures-having-a-mammogram.
4. Agnantis N J, Goussia A C, Stefanou D. Tumor markers. An update approach for their prognostic significance. Part I. In Vivo. 2003; 17(6):609-18. PubMed PMID: 14758728.
5. Arciero C, Somiari S B, Shriver C D, Brzeski H, Jordan R, Hu H, et al. Functional relationship and gene ontology classification of breast cancer biomarkers. Int J Biol Markers. 2003; 18(4):241-72. PubMed PMID: 14756541.
6. Bernoux A, de Cremoux P, Laine-Bidron C, Martin E C, Asselain B, Magdelenat H. Estrogen receptor negative and progesterone receptor positive primary breast cancer: pathological characteristics and clinical outcome. Institut Curie Breast Cancer Study Group. Breast Cancer Res Treat. 1998; 49(3):219-25. PubMed PMID: 9776505.
7. Dowsett M, Cooke T, Ellis I, Gullick W J, Gusterson B, Mallon E, et al. Assessment of HER2 status in breast cancer: why, when and how? Eur J Cancer. 2000; 36(2): 170-6. PubMed PMID: 10741274.
8. Shak S. Overview of the trastuzumab (Herceptin) anti-HER2 monoclonal antibody clinical program in HER2-overexpressing metastatic breast cancer. Herceptin Multinational Investigator Study Group. Semin Oncol. 1999; 26(4 Suppl 12):71-7. PubMed PMID: 10482196.
9. Slamon D J, Clark G M, Wong S G, Levin W J, Ullrich A, McGuire W L. Human breast cancer: correlation of relapse and survival with amplification of the HER-2/neu oncogene. Science. 1987; 235(4785):177-82. PubMed PMID: 3798106.
10. Slamon D J, Godolphin W, Jones L A, Holt J A, Wong S G, Keith D E, et al. Studies of the HER-2/neu proto-oncogene in human breast and ovarian cancer. Science. 1989; 244(4905):707-12. PubMed PMID: 2470152.
11. Kaklamani V. A genetic signature can predict prognosis and response to therapy in breast cancer: Oncotype DX. Expert review of molecular diagnostics. 2006; 6(6):803-9. Epub 2006 Dec. 5. doi: 10.1586/14737159.6.6.803. PubMed PMID: 17140367.
12. Manjili M H, Najarian K, Wang X Y. Signatures of tumor-immune interactions as biomarkers for breast cancer prognosis. Future Oncol. 2012; 8(6):703-11. Epub 2012 Jul. 7. doi: 10.2217/fon.12.57. PubMed PMID: 22764768.
13. Reuschenbach M, von Knebel Doeberitz M, Wentzensen N. A systematic review of humoral immune responses against tumor antigens. Cancer immunology, immunotherapy: CII. 2009; 58(10):1535-44. Epub 2009 Jun. 30. doi: 10.1007/s00262-009-0733-4. PubMed PMID: 19562338; PubMed Central PMCID: PMC2782676.
14. Casiano C A, Mediavilla-Varela M, Tan E M. Tumor-associated antigen arrays for the serological diagnosis of cancer. Mol Cell Proteomics. 2006; 5(10):1745-59. Epub 2006 May 31. doi: R600010-MCP200 [pii] 10.1074/mcp.R600010-MCP200. PubMed PMID: 16733262.
15. Lu H, Goodell V, Disis M L. Humoral Immunity Directed against Tumor-Associated Antigens As Potential Biomarkers for the Early Diagnosis of Cancer. J Proteome Res. 2008; 7(4):1388-94. PubMed PMID: 18311901.
16. Desmetz C, Mange A, Maudelonde T, Solassol J. Autoantibody signatures: progress and perspectives for early cancer detection. Journal of cellular and molecular medicine. 2011; 15(10):2013-24. Epub 2011 Jun. 10. doi: 10.1111/j.1582-4934.2011.01355.x. PubMed PMID: 21651719.
17. Piura E, Piura B. Autoantibodies to tailor-made panels of tumor-associated antigens in breast carcinoma. Journal of oncology. 2011; 2011:982425. Epub 2011 Mar. 23. doi: 10.1155/2011/982425. PubMed PMID: 21423545; PubMed Central PMCID: PMC3056218.
18. Piura E, Piura B. Autoantibodies to tumor-associated antigens in breast carcinoma. Journal of oncology. 2010; 2010:264926. Epub 2010 Nov. 30. doi: 10.1155/2010/264926. PubMed PMID: 21113302; PubMed Central PMCID: PMC2989457.
19. Finn O J. Immune response as a biomarker for cancer detection and a lot more. N Engl J Med. 2005; 353(12): 1288-90. PubMed PMID: 16177255.
20. Pavoni E, Pucci A, Vaccaro P, Monteriu G, Ceratti Ade P, Lugini A, et al. A study of the humoral immune response of breast cancer patients to a panel of human tumor antigens identified by phage display. Cancer Detect Prev. 2006; 30(3):248-56. PubMed PMID: 16876336.
21. Sioud M, Hansen M H. Profiling the immune response in patients with breast cancer by phage-displayed cDNA libraries. Eur J Immunol. 2001; 31(3):716-25. PubMed PMID: 11241275.
22. Storr S J, Chakrabarti J, Barnes A, Murray A, Chapman C J, Robertson J F. Use of autoantibodies in breast cancer screening and diagnosis. Expert Rev Anticancer Ther. 2006; 6(8):1215-23. PubMed PMID: 16925487.
23. Tan E M, Shi F D. Relative paradigms between autoantibodies in lupus and autoantibodies in cancer. Clin Exp Immunol. 2003; 134(2):169-77. PubMed PMID: 14616773.
24. Barlow D J, Edwards M S, Thornton J M. Continuous and discontinuous protein antigenic determinants. Nature. 1986; 322(6081):747-8. PubMed PMID: 2427953.
25. Laver W G, Air G M, Webster R G, Smith-Gill S J. Epitopes on protein antigens: misconceptions and realities. Cell. 1990; 61(4):553-6. PubMed PMID: 1693095.
26. Ramachandran N, Hainsworth E, Bhullar B, Eisenstein S, Rosen B, Lau A Y, et al. Self-assembling protein microarrays. Science. 2004; 305(5680):86-90. Epub 2004 Jul. 3. doi: 10.1126/science.1097639 305/5680/86 [pii]. PubMed PMID: 15232106.
27. Ehrlich J R, Qin S, Liu B C. The 'reverse capture' autoantibody microarray: a native antigen-based platform for autoantibody profiling. Nature protocols. 2006; 1(1): 452-60. Epub 2007 Apr. 5. doi: 10.1038/nprot.2006.66. PubMed PMID: 17406268.
28. Tan H T, Low J, Lim S G, Chung M C. Serum autoantibodies as biomarkers for early cancer detection. The FEBS journal. 2009; 276(23):6880-904. Epub 2009 Oct. 29. doi: 10.1111/j.1742-4658.2009.07396.x. PubMed PMID: 19860826.
29. Egland K A, Vincent J J, Strausberg R, Lee B, Pastan I. Discovery of the breast cancer gene BASE using a molecular approach to enrich for genes encoding membrane and secreted proteins. Proc Natl Acad Sci USA. 2003; 100(3):1099-104. PubMed PMID: 12538848.
30. Boyle J S, Koniaras C, Lew A M. Influence of cellular location of expressed antigen on the efficacy of DNA vaccination: cytotoxic T lymphocyte and antibody responses are suboptimal when antigen is cytoplasmic after intramuscular DNA immunization. Int Immunol. 1997; 9(12):1897-906. PubMed PMID: 9466317.
31. Drew D R, Lightowlers M, Strugnell R A. Humoral immune responses to DNA vaccines expressing secreted, membrane bound and non-secreted forms of the Tania ovis 45W antigen. Vaccine. 2000; 18(23):2522-32. PubMed PMID: 10775786.
32. Bendtsen J D, Nielsen H, von Heijne G, Brunak S. Improved prediction of signal peptides: SignalP 3.0. J Mol Biol. 2004; 340(4):783-95. doi: 10.1016/j.jmb.2004.05.028. PubMed PMID: 15223320.
33. Nielsen H, Engelbrecht J, Brunak S, von Heijne G. Identification of prokaryotic and eukaryotic signal peptides and prediction of their cleavage sites. Protein engineering. 1997; 10(1):1-6. PubMed PMID: 9051728.
34. Krogh A, Larsson B, von Heijne G, Sonnhammer E L. Predicting transmembrane protein topology with a hidden Markov model: application to complete genomes. J Mol Biol. 2001; 305(3):567-80. doi: 10.1006/jmbi.2000.4315. PubMed PMID: 11152613.
35. Bergstralh E J, Kosanke J L. Computerized matching of cases to controls. Rochester, Minn.: Mayo Clinic Department of Health Science Research, 1995.
36. Hosmer D W, Lemeshow S. Goodness of fit tests for the multiple logistic regression model. Communications in Statistics—Theory and Methods: Taylor & Francis Group; 1980. p. 1043-69.
37. Akaike H. Information Theory and an Extension of the Maximum Likelihood Principle. In: Kotz S, Johnson N L, editors. Breakthroughs in Statistics. Springer Series in Statistics: Springer New York; 1992. p. 610-24.
38. Neve R M, Chin K, Fridlyand J, Yeh J, Baehner F L, Fevr T, et al. A collection of breast cancer cell lines for the study of functionally distinct cancer subtypes. Cancer Cell. 2006; 10(6):515-27. Epub 2006 Dec. 13. doi: 10.1016/j.ccr.2006.10.008. PubMed PMID: 17157791; PubMed Central PMCID: PMC2730521.

39. Kotera Y, Fontenot J D, Pecher G, Metzgar R S, Finn O J. Humoral immunity against a tandem repeat epitope of human mucin MUC-1 in sera from breast, pancreatic, and colon cancer patients. Cancer Res. 1994; 54(11):2856-60. Epub 1994 Jun. 1. PubMed PMID: 7514493.

40. von Mensdorff-Pouilly S, Gourevitch M M, Kenemans P, Verstraeten A A, Litvinov S V, van Kamp G J, et al. Humoral immune response to polymorphic epithelial mucin (MUC-1) in patients with benign and malignant breast tumours. Eur J Cancer. 1996; 32A(8):1325-31. Epub 1996 Jul. 1. PubMed PMID: 8869094.

41. Disis M L, Pupa S M, Gralow J R, Dittadi R, Menard S, Cheever M A. High-titer HER-2/neu protein-specific antibody can be detected in patients with early-stage breast cancer. J Clin Oncol. 1997; 15(11):3363-7. Epub 1997 Nov. 18. PubMed PMID: 9363867.

42. Ladd J J, Chao T, Johnson M M, Qiu J, Chin A, Israel R, et al. Autoantibody signatures involving glycolysis and splicesome proteins precede a diagnosis of breast cancer among postmenopausal women. Cancer Res. 2013; 73(5): 1502-13. Epub 2012 Dec. 28. doi: 10.1158/0008-5472.CAN-12-2560. PubMed PMID: 23269276.

43. Perou C M, Sorlie T, Eisen M B, van de Rijn M, Jeffrey S S, Rees C A, et al. Molecular portraits of human breast tumours. Nature. 2000; 406(6797):747-52. Epub 2000/08/30. doi: 10.1038/35021093. PubMed PMID: 10963602.

44. Lacombe J, Mange A, Jarlier M, Bascoul-Mollevi C, Rouanet P, Lamy P J, et al. Identification and validation of new autoantibodies for the diagnosis of DCIS and node negative early-stage breast cancers. Int J Cancer. 2013; 132(5):1105-13. Epub 2012 Aug. 14. doi: 10.1002/ijc.27766. PubMed PMID: 22886747.

45. Mange A, Lacombe J, Bascoul-Mollevi C, Jarlier M, Lamy P J, Rouanet P, et al. Serum autoantibody signature of ductal carcinoma in situ progression to invasive breast cancer. Clin Cancer Res. 2012; 18(7):1992-2000. Epub 2012 Feb. 11. doi: 10.1158/1078-0432.CCR-11-2527. PubMed PMID: 22322670.

46. Ye H, Sun C, Ren P, Dai L, Peng B, Wang K, et al. Mini-array of multiple tumor-associated antigens (TAAs) in the immunodiagnosis of breast cancer. Oncology letters. 2013; 5(2):663-8. Epub 2013 Feb. 20. doi: 10.3892/ol.2012.1062. PubMed PMID: 23420714; PubMed Central PMCID: PMC3573153.

47. Gion M, Mione R, Leon A E, Dittadi R. Comparison of the diagnostic accuracy of CA27.29 and CA15.3 in primary breast cancer. Clin Chem. 1999; 45(5):630-7. Epub 1999 May 1. PubMed PMID: 10222349.

---

We claim:

1. A composition consisting of between 2 and 25 proteins, or antigenic fragments thereof, wherein the between 2 and 25 proteins or antigenic fragments thereof include at least (i) ANGPTL4 or an ANGPTL4 antigenic fragment, and (ii) DKK1 or a DKK1 antigenic fragment, wherein:
    (a) the proteins, or antigenic fragments thereof are detectably labeled; and/or
    (b) the proteins, or antigenic fragments thereof are immobilized on a surface, wherein no additional proteins or antigenic fragments thereof are present on the surface.

2. The composition of claim 1, wherein the between 2 and 25 proteins or antigenic fragments thereof include at least one proteins selected from the group consisting of ANGPTL4, DKK1, EPHA2, GAL1, LAMC2, SPON2, CST2, SPINT2 and SSR2, or antigenic fragments thereof.

3. The composition of claim 1, wherein the between 2 and 25 proteins or antigenic fragments thereof include at least three proteins selected from the group consisting of EPHA2, LAMC2, SPON2, SSR2, GAL1, GFRA1, LRRC15, CD147, CD320, CDH3, LRP10, SPINT2, SUSD2, and CST2, or antigenic fragments thereof.

4. The composition of claim 1, wherein the between 2 and 25 proteins or antigenic fragments include one or both of MUC1 protein and GRN protein, or antigenic fragments thereof.

5. The composition of claim 1, wherein the composition consists of between 2 and 20 proteins, or antigenic fragments thereof.

6. The composition of claim 1, wherein the composition consists of between 4 and 10 proteins, or antigenic fragments thereof.

7. The composition of claim 1, wherein the composition consists of between 5 and 10 proteins, or antigenic fragments thereof.

8. The composition of claim 1, wherein the composition includes proteins, or antigenic fragments thereof selected from one of the following sets:
    ANGPTL4, DKK1, GAL1, GFRA1, GRANULIN, LRRC15, and MUC1;
    ANGPTL4, DKK1, GAL1, GRANULIN, LRRC15, and MUC1;
    ANGPTL4, DKK1, GAL1, and LRRC15;
    ANGPTL4, DKK1, GAL1, GFRA1, and LRRC15;
    ANGPTL4, DKK1, GAL1, GFRA1, GRANULIN, and LRRC15;
    ANGPTL4, DKK1, GAL1, GRANULIN, and LRRC15; and
    ANGPTL4, DKK1, GAL1, LRRC15, and MUC1.

9. The composition of claim 1, wherein the composition includes ANGPTL4, DKK1, GAL1, MUC1, GFRA1, GRN and LRRC15 proteins, or antigenic fragments thereof.

10. The composition of claim 1, wherein the between 2 and 25 proteins, or antigenic fragments thereof comprise native extracellular domains and/or native secreted proteins or antigenic fragments thereof.

11. The composition of claim 1, wherein the proteins, or antigenic fragments thereof are detectably labeled.

12. The composition of claim 1, wherein the proteins, or antigenic fragments thereof are immobilized on a surface.

13. The composition of claim 2, wherein the between 2 and 25 proteins, or antigenic fragments thereof comprise native extracellular domains and/or native secreted proteins or antigenic fragments thereof.

14. The composition of claim 2, wherein the proteins, or antigenic fragments thereof are detectably labeled.

15. The composition of claim 2, wherein the proteins, or antigenic fragments thereof are immobilized on a surface.

16. The composition of claim 8, wherein the between 2 and 25 proteins, or antigenic fragments thereof comprise native extracellular domains and/or native secreted proteins or antigenic fragments thereof.

17. The composition of claim 8, wherein the proteins, or antigenic fragments thereof are detectably labeled.

18. The composition of claim 8, wherein the proteins, or antigenic fragments thereof are immobilized on a surface.

19. The composition of claim 1, wherein the between 2 and 25 proteins, or antigenic fragments thereof comprise native extracellular domains and/or native secreted proteins or antigenic fragments thereof, and wherein the proteins, or antigenic fragments thereof are immobilized on a surface.

20. The composition of claim 2, wherein the between 2 and 25 proteins, or antigenic fragments thereof comprise native extracellular domains and/or native secreted proteins or antigenic fragments thereof, and wherein the proteins, or antigenic fragments thereof are immobilized on a surface.

21. The composition of claim 8, wherein the between 2 and 25 proteins, or antigenic fragments thereof comprise native extracellular domains and/or native secreted proteins or antigenic fragments thereof, and wherein the proteins, or antigenic fragments thereof are immobilized on a surface.

\* \* \* \* \*